US010046116B2

(12) United States Patent
Bennison et al.

(10) Patent No.: US 10,046,116 B2
(45) Date of Patent: Aug. 14, 2018

(54) PROCESS AND DEVICE FOR DELIVERY OF FLUID BY CHEMICAL REACTION

(71) Applicant: Eli Lilly and Company, Indianapolis, IN (US)

(72) Inventors: Corrie Bennison, Lewis Center, OH (US); Christopher H. Muenzer, Columbus, OH (US); Timothy M. Blum, Columbus, OH (US); Christopher P. McKenzie, Lancaster, OH (US); Steven M. Madland, Gahanna, OH (US); Jeffrey L. Ellis, Gahanna, OH (US); Amy M. Heintz, Dublin, OH (US); Brian J. Kaseman, Summerville, SC (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/091,863

(22) Filed: Apr. 6, 2016

(65) Prior Publication Data

US 2016/0213847 A1   Jul. 28, 2016

Related U.S. Application Data

(62) Division of application No. 14/054,567, filed on Oct. 15, 2013, now Pat. No. 9,321,581.
(Continued)

(51) Int. Cl.
*A61M 5/20* (2006.01)
*B65D 83/64* (2006.01)
(Continued)

(52) U.S. Cl.
CPC ...... *A61M 5/2046* (2013.01); *A61M 5/14526* (2013.01); *A61M 5/155* (2013.01);
(Continued)

(58) Field of Classification Search
CPC ........... A61M 2005/14204; A61M 2005/2026; A61M 5/14526; A61M 5/155;
(Continued)

(56) References Cited

U.S. PATENT DOCUMENTS 2,390,246 A   12/1945 Folkman
2,923,243 A   2/1960 Crockford et al.
(Continued)

FOREIGN PATENT DOCUMENTS

DE   3809482   10/1989
EP   2221076   8/2010
(Continued)

OTHER PUBLICATIONS

Good, Brian T., et al., "An Effervescent Reaction Micropump for Portable Microfluidic Systems," Lab Chip, Jun. 2006, 659-66.
(Continued)

*Primary Examiner* — Patrick M Buechner
*Assistant Examiner* — Bob Zadeh
(74) *Attorney, Agent, or Firm* — Jonathan Anderson

(57) ABSTRACT

Processes and devices for delivering a fluid by chemical reaction are disclosed. A chemical reaction is initiated in a reaction chamber to produce a gas, and the gas acts upon a piston to deliver the fluid. An exemplary device may include an upper chamber, a lower chamber, a fluid chamber, a piston between the lower chamber and the fluid chamber, and a one-way valve between the upper chamber and the lower chamber.

13 Claims, 24 Drawing Sheets

Related U.S. Application Data

(60) Provisional application No. 61/713,236, filed on Oct. 12, 2012, provisional application No. 61/713,250, filed on Oct. 12, 2012.

(51) Int. Cl.
  *A61M 5/145* (2006.01)
  *A61M 5/155* (2006.01)
  *B65D 83/60* (2006.01)
  *B65D 83/14* (2006.01)
  *A61M 5/142* (2006.01)

(52) U.S. Cl.
  CPC ... *B65D 83/64* (2013.01); *A61M 2005/14204* (2013.01); *A61M 2005/2026* (2013.01); *B65D 83/14* (2013.01); *B65D 83/60* (2013.01); *B65D 83/643* (2013.01)

(58) Field of Classification Search
  CPC ..... A61M 5/2046; B65D 83/14; B65D 83/60; B65D 83/64; B65D 83/643
  See application file for complete search history.

(56) References Cited

U.S. PATENT DOCUMENTS

| | | | |
|---|---|---|---|
| 3,405,845 | A * | 10/1968 | Cook .................... B05C 17/015 222/387 |
| 3,467,526 | A | 9/1969 | Mitchell et al. |
| 4,031,889 | A | 6/1977 | Pike |
| 4,744,786 | A * | 5/1988 | Hooven ................ A61M 5/155 128/DIG. 12 |
| 4,785,972 | A | 11/1988 | LeFevre |
| 5,062,834 | A * | 11/1991 | Gross .................... A61M 5/155 604/143 |
| 5,151,093 | A | 9/1992 | Theeuwes et al. |
| 5,167,641 | A | 12/1992 | Schmitz |
| 5,304,128 | A | 4/1994 | Haber et al. |
| 5,312,389 | A * | 5/1994 | Theeuwes ........... A61M 5/1452 222/389 |
| 5,398,850 | A | 3/1995 | Sancoff et al. |
| 5,518,145 | A * | 5/1996 | Chen ........................ B05C 7/00 222/1 |
| 5,540,665 | A * | 7/1996 | Mercado ........... A61M 5/14526 604/145 |
| 5,645,824 | A | 7/1997 | Lim et al. |
| 5,700,245 | A | 12/1997 | Sancoff et al. |
| 5,858,001 | A | 1/1999 | Tsals et al. |
| 5,871,125 | A | 2/1999 | Gross |
| 5,891,087 | A * | 4/1999 | Ohtani .................. A61M 5/284 604/190 |
| 5,941,857 | A | 8/1999 | Nguyen et al. |
| 5,992,700 | A | 11/1999 | McGlothlin et al. |
| 6,086,568 | A | 7/2000 | Caizza |
| 6,086,569 | A | 7/2000 | Schweizer |
| 6,156,014 | A | 12/2000 | Petersen et al. |
| 6,270,479 | B1 | 8/2001 | Bergens et al. |
| 6,431,468 | B1 | 8/2002 | Brown et al. |
| 6,575,961 | B2 * | 6/2003 | Joshi .................. A61M 5/14244 424/438 |
| 6,830,560 | B1 * | 12/2004 | Gross .................. A61M 5/2046 604/143 |
| 6,913,593 | B1 | 7/2005 | Alexandre et al. |
| 6,964,356 | B2 | 11/2005 | Kim |
| 7,632,245 | B1 | 12/2009 | Cowan et al. |
| 7,753,884 | B2 | 7/2010 | Gallnböck |
| 7,988,663 | B2 | 8/2011 | Schiller et al. |
| 8,157,769 | B2 | 4/2012 | Cabiri |
| 8,353,426 | B2 * | 1/2013 | Wold .................... B05B 11/025 222/1 |
| 8,353,679 | B2 | 1/2013 | Yamamoto et al. |
| 9,321,581 | B2 * | 4/2016 | Bennison ............... B65D 83/64 |
| 2001/0025168 | A1 | 9/2001 | Gross et al. |
| 2001/0050085 | A1 | 12/2001 | Knudson et al. |
| 2002/0156461 | A1 * | 10/2002 | Joshi ................. A61M 5/14244 604/891.1 |
| 2003/0168480 | A1 | 9/2003 | Kim |
| 2004/0249339 | A1 | 12/2004 | Willis et al. |
| 2005/0006401 | A1 | 1/2005 | Kim |
| 2005/0187522 | A1 | 8/2005 | Miller |
| 2006/0235264 | A1 | 10/2006 | Vassallo |
| 2007/0228071 | A1 | 10/2007 | Kamen et al. |
| 2008/0066766 | A1 | 3/2008 | Paraschac et al. |
| 2009/0093787 | A1 | 4/2009 | Barbour |
| 2009/0131860 | A1 | 5/2009 | Nielsen |
| 2009/0227942 | A1 | 9/2009 | Stroem Hansen et al. |
| 2009/0259176 | A1 | 10/2009 | Yairi |
| 2009/0259179 | A1 | 10/2009 | Hillios et al. |
| 2010/0030152 | A1 | 2/2010 | Lee et al. |
| 2010/0069846 | A1 | 3/2010 | Stamp |
| 2010/0137808 | A1 | 6/2010 | Wilmot et al. |
| 2010/0174225 | A1 | 7/2010 | Pesach et al. |
| 2011/0054390 | A1 | 3/2011 | Searle et al. |
| 2011/0092906 | A1 * | 4/2011 | Bottger ............... A61M 5/2046 604/143 |
| 2011/0272271 | A1 | 11/2011 | Hong et al. |
| 2012/0078216 | A1 | 3/2012 | Smith et al. |
| 2014/0103075 | A1 * | 4/2014 | Bennison ............... B65D 83/64 222/389 |
| 2015/0314070 | A1 * | 11/2015 | Heintz ................. A61M 5/2046 222/1 |
| 2016/0213846 | A1 * | 7/2016 | Bennison ............... B65D 83/64 |
| 2016/0213847 | A1 * | 7/2016 | Bennison ............... B65D 83/64 |

FOREIGN PATENT DOCUMENTS

| | | |
|---|---|---|
| EP | 2489387 | 8/2012 |
| WO | 92019571 | 11/1992 |
| WO | 95001198 | 1/1995 |
| WO | 95023641 | 9/1995 |
| WO | 97028750 | 8/1997 |
| WO | 99012593 | 3/1999 |
| WO | 99022790 | 5/1999 |
| WO | 99062576 | 12/1999 |
| WO | 01000270 | 1/2001 |
| WO | 07071485 | 6/2007 |
| WO | 09116045 | 9/2009 |
| WO | 09144726 | 12/2009 |
| WO | 14059444 | 4/2014 |

OTHER PUBLICATIONS

"Development of an On-Demand, Generic, Drug-Delivery System," Southern Research Institute, 2000 Ninth Avenue South, Birmingham, AL 35255-5305 Aug. 6, 1985.

* cited by examiner

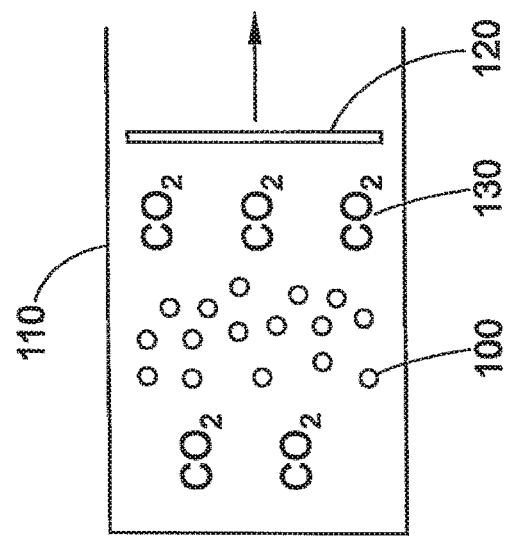
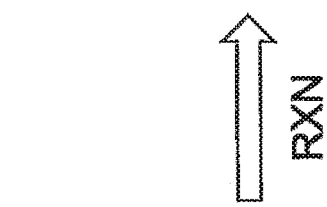
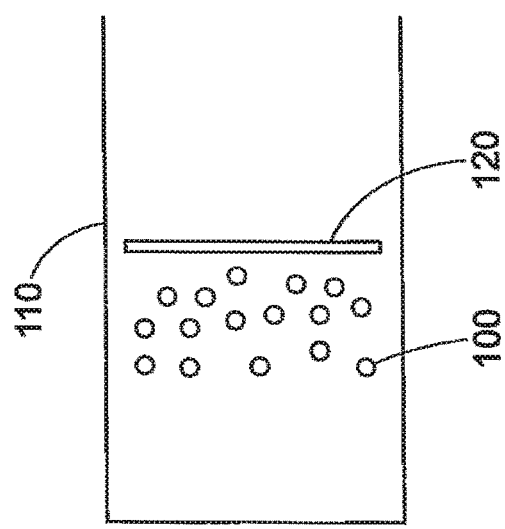
FIG. 1

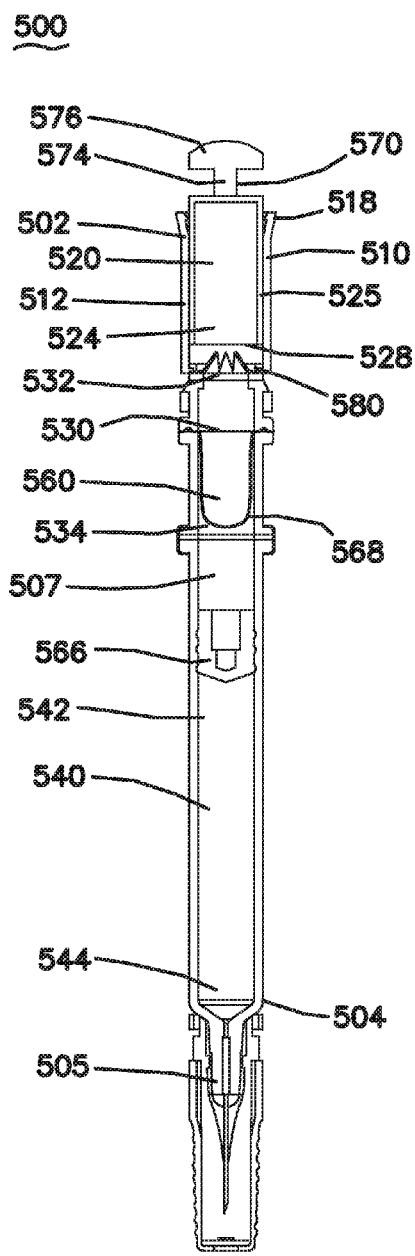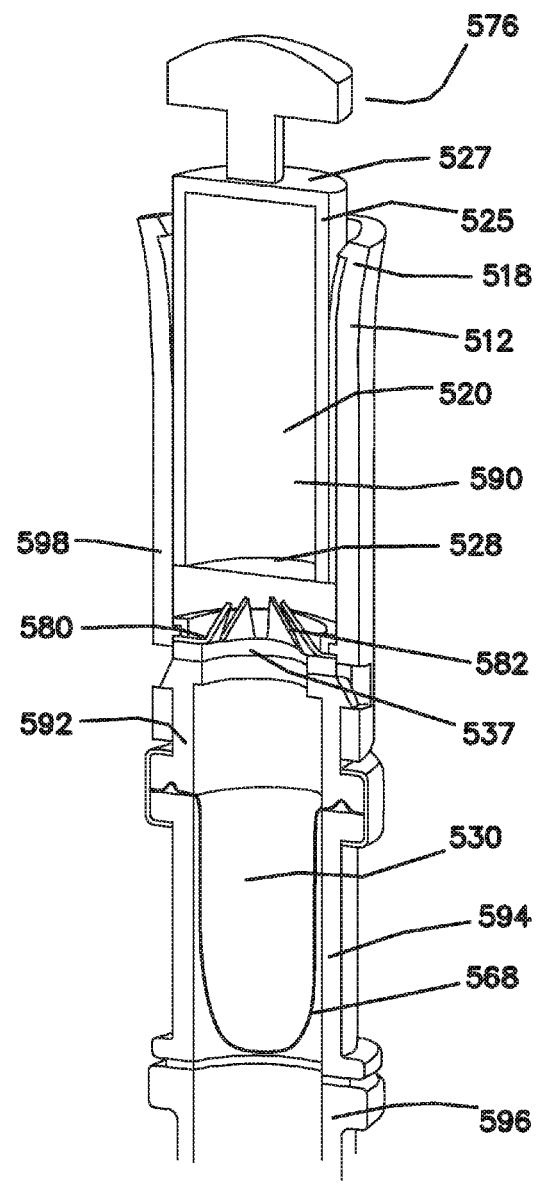
FIG. 9
FIG. 10

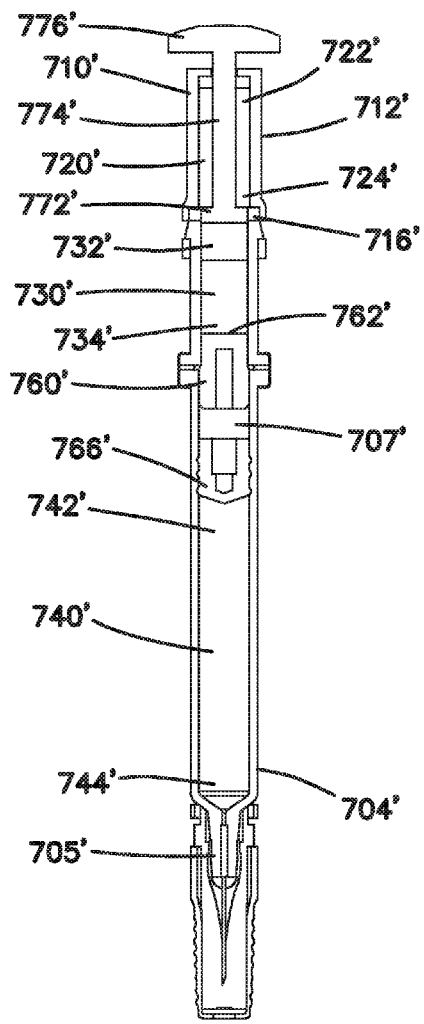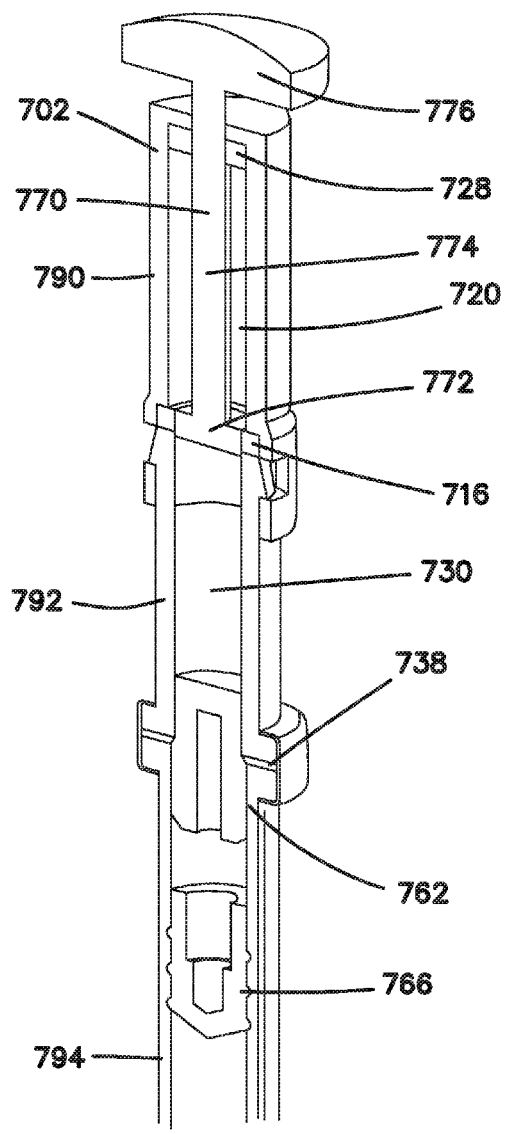

PROCESS AND DEVICE FOR DELIVERY OF FLUID BY CHEMICAL REACTION

RELATED APPLICATIONS

This application is a divisional of U.S. patent application Ser. No. 14/054,567, filed Oct. 15, 2013, and claims priority to U.S. Provisional Application Nos. 61/713,236 and 61/713,250, both filed Oct. 12, 2012, all of which are expressly incorporated herein by reference as if reproduced in full below.

BACKGROUND

The present disclosure relates to processes and devices for parenteral delivery of high-viscosity fluids, e.g., protein therapeutics, by a chemical reaction that generates a gas.

Protein therapeutics is an emerging class of drug therapy that promises to provide treatment for a broad range of diseases, such as autoimmune disorders, cardiovascular diseases, and cancer. The dominant delivery method for protein therapeutics, particularly monoclonal antibodies, is through intravenous infusion, in which large volumes of dilute solutions are delivered over time. Intravenous infusion usually requires the supervision of a doctor or nurse and is performed in a clinical setting. This can be inconvenient for a patient, and so efforts are being made to permit the delivery of protein therapeutics at home. Desirably, a protein therapeutic formulation can be administered using a syringe for subcutaneous delivery instead of requiring intravenous administration. Subcutaneous injections are commonly administered by laypersons, for example in the administration of insulin by diabetics.

Transitioning therapeutic protein formulations from intravenous delivery to injection devices like syringes requires addressing challenges associated with delivering high concentrations of high molecular weight molecules in a manner that is easy, reliable, and causes minimal pain to the patient. In this regard, while intravenous bags typically have a volume of 1 liter, the standard volume for a syringe ranges from 0.3 milliliters up to 25 milliliters. Thus, depending on the drug, to deliver the same amount of therapeutic proteins, the concentration may have to increase by a factor of 40 or more. Also, injection therapy is moving towards smaller needle diameters and faster delivery times for purposes of patient comfort and compliance.

Delivery of protein therapeutics is also challenging because of the high viscosity associated with such therapeutic formulations, and the high forces needed to push such formulations through a parenteral device. Formulations with absolute viscosities above 40-60 centipoise (cP) are very difficult to deliver by conventional spring driven auto-injectors for multiple reasons. Structurally, the footprint of a spring for the amount of pressure delivered is relatively large and fixed to specific shapes, which reduces flexibility of design for delivery devices. Next, auto-injectors are usually made of plastic parts. However, a large amount of energy must be stored in the spring to reliably deliver high-viscosity fluids. This may cause damage to the plastic parts due to creep, which is the tendency of the plastic part to permanently deform under stress. An auto-injector typically operates by using the spring to push a needle-containing internal component towards an outer edge of the housing of the syringe. There is risk of breaking the syringe when the internal component impacts the housing, due to the high applied force needed to inject a high-viscosity fluid. Also, the sound associated with the impact can cause patient anxiety, reducing future compliance. The generated pressure versus time profile of such a spring driven auto-injector cannot be readily modified, which prevents users from fine tuning pressure to meet their delivery needs.

It would be desirable to provide processes and devices by which a high-viscosity fluid could be self-administered in a reasonable time and with a limited injection space. These processes and devices could be used to deliver high-concentration protein, or other high viscosity pharmaceutical formulations.

SUMMARY

Disclosed in various embodiments are processes and devices for delivery of a high-viscosity fluid using a gas-generating chemical reaction. Generally, one or more reagents are reacted to generate a gas. The gas is used to push a piston inside a syringe, delivering the contents of the syringe to the patient/user.

Disclosed in some embodiments is a device for delivering a fluid by chemical reaction, comprising: a reagent chamber having a plunger at an upper end and a one-way valve at a lower end, the one-way valve permitting exit from the reagent chamber; a reaction chamber having the one-way valve at an upper end and a piston at a lower end; and a fluid chamber having the piston at an upper end, wherein the piston moves in response to pressure generated in the reaction chamber such that the volume of the reaction chamber increases and the volume of the fluid chamber decreases.

The reaction chamber may have a volume of at most 1 $cm^3$. The fluid chamber may contain a high-viscosity fluid having an absolute viscosity of from about 5 centipoise to about 1000 centipoise, or a viscosity of at least 40 centipoise. The reagent chamber may contain a solvent and a bicarbonate powder dissolved in the solvent. The solvent can comprise water. The reaction chamber may contain a dry acid powder and a release agent. In particular embodiments, the acid powder is citrate and the release agent is sodium chloride. Alternatively, the reaction chamber can contain at least one or at least two chemical reagents that react with each other to generate a gas. Separately, the reaction chamber may further comprise a release agent.

In some alternative embodiments, an upper chamber may contain a solvent. The lower chamber may contain at least two chemical reagents that react with each other to generate a gas. The lower chamber may contain a bicarbonate powder and an acid powder.

The piston of the device may be formed from a push surface at the lower end of the reaction chamber, a stopper at the upper end of the fluid chamber, and a rod connecting the push surface and the stopper.

A plunger may include a thumbrest, as well as a pressure lock that cooperates with the upper chamber to lock the plunger in place after being depressed. The pressure lock can be proximate the thumbrest and cooperate with an upper surface of the upper chamber.

The lower chamber may be defined by the one-way valve, a continuous sidewall, and the piston, the one-way valve and the sidewall being fixed relative to each other such that the volume of the lower chamber changes only through movement of the piston.

In particular embodiments, the upper chamber, the lower chamber, and the fluid chamber are cylindrical and are coaxial. In others, the upper chamber, the lower chamber, and the fluid chamber are separate pieces that are joined together to make the device. The one-way valve can feed a balloon in the lower chamber, the balloon pushing the piston. Sometimes, either the upper chamber or the lower chamber contains an encapsulated reagent.

Also described in various embodiments is a device for delivering a fluid by chemical reaction, comprising: an upper chamber having a seal at a lower end; a lower chamber having a port at an upper end, a ring of teeth at the upper end having the teeth oriented towards the seal of the upper chamber, and a piston at a lower end; and a fluid chamber having the piston at an upper end; wherein the upper chamber moves axially relative to the lower chamber; and wherein the piston moves in response to pressure generated in the lower chamber such that the volume of the reaction chamber increases and the volume of the fluid chamber decreases.

The piston may include a head and a balloon that communicates with the port. The ring of teeth may surround the port. The upper chamber may travel within a barrel of the device. Sometimes, the upper chamber is the lower end of a plunger. The plunger may include a pressure lock that cooperates with a top end of the device to lock the upper chamber in place after being depressed. Alternatively, the top end of the device can include a pressure lock that cooperates with a top surface of the upper chamber to lock the upper chamber in place when moved sufficiently towards the lower chamber.

The fluid chamber may contain a high-viscosity fluid having a viscosity of at least 40 centipoise. The upper chamber may contain a solvent. The lower chamber may contain at least two chemical reagents that react with each other to generate a gas. Sometimes, the upper chamber, the lower chamber, and the fluid chamber are separate pieces that are joined together to make the device. In yet other embodiments, either the upper chamber or the lower chamber contains an encapsulated reagent.

Also described herein is a device for delivering a fluid by chemical reaction, comprising: an upper chamber, a lower chamber having a piston at a lower end; a fluid chamber having the piston at an upper end; and a plunger comprising a shaft that runs through the upper chamber, a stopper at a lower end of the shaft, and a thumbrest at an upper end of the shaft, the stopper cooperating with a seat to separate the upper chamber and the lower chamber, wherein pulling the plunger causes the stopper to separate from the seat and create fluid communication between the upper chamber and the lower chamber; and wherein the piston moves in response to pressure generated in the lower chamber such that the volume of the reaction chamber increases and the volume of the fluid chamber decreases.

The fluid chamber may contain a high-viscosity fluid having a viscosity of at least 40 centipoise. The upper chamber may contain a solvent. The lower chamber may contain at least two chemical reagents that react with each other to generate a gas. Sometimes, the upper chamber, the lower chamber, and the fluid chamber are separate pieces that are joined together to make the device. In yet other embodiments, either the upper chamber or the lower chamber contains an encapsulated reagent.

The present disclosure also relates to a device for delivering a fluid by chemical reaction, comprising: a reaction chamber divided by a barrier into a first compartment and a second compartment, the first compartment containing at least two dry chemical reagents that can react with each other to generate a gas, and the second compartment containing a solvent; and a fluid chamber having an outlet; wherein fluid in the fluid chamber exits through the outlet in response to pressure generated in the reaction chamber.

The pressure generated in the reaction chamber may act on a piston in the fluid chamber to cause fluid to exit through the outlet.

In some embodiments, the reaction chamber is formed from a sidewall, the fluid chamber is formed from a sidewall, and the reaction chamber and the fluid chamber are fluidly connected at a first end of the device.

In other embodiments, the reaction chamber includes a flexible wall, proximate to the fluid chamber; and wherein the fluid chamber is formed from a flexible sidewall, such that pressure generated in the reaction chamber causes the flexible wall to expand and compress the flexible sidewall of the fluid chamber, causing fluid to exit through the outlet.

The reaction chamber and the fluid chamber may be surrounded by a housing. Sometimes, the reaction chamber and the fluid chamber are side-by-side in the housing. In other embodiments, a needle extends from a bottom of the housing and is fluidly connected to the outlet of the fluid chamber; and the reaction chamber is located on top of the fluid chamber.

The reaction chamber may be defined by the one-way valve, a sidewall, and the piston, the one-way valve and the sidewall being fixed relative to each other such that the volume of the reaction chamber changes only through movement of the piston.

Also disclosed in various embodiments is a device for dispensing a fluid by chemical reaction, comprising: a reaction chamber having first and second ends; a piston at a first end of the reaction chamber, the piston being operative to migrate within the device in response to a pressure generated in the reaction chamber; and a one-way valve at the second end of the reaction chamber permitting entry into the reaction chamber.

The reaction chamber may have a volume of at most 1 $cm^3$. The reaction chamber may contain a dry acid powder and a release agent. In particular embodiments, the acid powder is citrate and the release agent is sodium chloride. Alternatively, the reaction chamber can contain at least one or at least two chemical reagents that react with each other to generate a gas. Separately, the reaction chamber may further comprise a release agent.

The device may further comprise a fluid chamber containing the fluid to be dispensed, the piston being operative to decrease the volume of the fluid chamber in response to the pressure generated in the reaction chamber. The fluid chamber may contain a high-viscosity fluid having an absolute viscosity of from about 5 centipoise to about 1000 centipoise, or a viscosity of at least 40 centipoise.

The device may further comprise a reagent chamber on an opposite side of the one-way valve. The reagent chamber may contain a solvent and a bicarbonate powder dissolved in the solvent. The solvent can comprise water. The device may further comprise a plunger at an end of the reagent chamber opposite the one-way valve. The plunger may cooperate with the reagent chamber to lock the plunger in place after being depressed.

The piston may be formed from a push surface at the reaction chamber, a stopper, and a rod connecting the push surface and the stopper.

The reaction chamber can be defined by the one-way valve, a sidewall, and the piston, the one-way, valve and the sidewall being fixed relative to each other such that the volume of the reaction chamber changes only through movement of the piston.

Also disclosed in various embodiments is a device for delivering a fluid by chemical reaction, comprising: a barrel which is divided into a reagent chamber, a reaction chamber, and a fluid chamber by a one-way valve and a piston; and a plunger at one end of the reagent chamber; wherein the one-way valve is located between the reagent chamber and the reaction chamber; and wherein the piston separates the reaction chamber and the fluid chamber, the piston being moveable to change the volume ratio between the reaction chamber and the fluid chamber.

The present disclosure also relates to a device for delivering a fluid by chemical reaction, comprising: a barrel containing a reaction chamber and a fluid chamber which are separated by a moveable piston; and a thermal source for heating the reaction chamber.

The reaction chamber may contain at least one chemical reagent that generates a gas upon exposure to heat. The at least one chemical reagent can be 2,2'-azobisisobutyronitrile. The generated gas can be nitrogen gas.

The reaction chamber may have a volume of at most 1 $cm^3$. The fluid chamber may contain a high-viscosity fluid having an absolute viscosity of from about 5 centipoise to about 1000 centipoise, or a viscosity of at least 40 centipoise.

The present disclosure also describes a device for delivering a fluid by chemical reaction, comprising: a barrel containing a reaction chamber and a fluid chamber which are separated by a moveable piston; and a light source that illuminates the reaction chamber.

The reaction chamber may contain at least one chemical reagent that generates a gas upon exposure to light. The at least one chemical reagent can be silver chloride.

The reaction chamber may have a volume of at most 1 $cm^3$. The fluid chamber may contain a high-viscosity fluid having an absolute viscosity of from about 5 centipoise to about 1000 centipoise, or a viscosity of at least 40 centipoise.

Also described herein in various embodiments is a process for delivering a high-viscosity fluid by chemical reaction, comprising: initiating a gas-generating chemical reaction in a reaction chamber of a device, the chamber including a piston; wherein the gas moves the piston into a fluid chamber containing the high-viscosity fluid and delivers the high-viscosity fluid; and wherein the high-viscosity fluid is delivered with a constant pressure versus time profile.

The initiating can be performed by dissolving at least two different chemical reagents in a solvent. The at least two chemical reagents can include a chemical compound having a first dissolution rate and the same chemical compound having a second different dissolution rate. The dissolution rates can be obtained by changing the surface area of the chemical compound, or by encapsulating the chemical compound with a coating to obtain the different dissolution rate.

The pressure versus time profile may include a burst.

The reaction chamber may contain a dry acid reagent, with a solvent containing a predissolved bicarbonate being added to the reaction chamber from a reagent chamber on an opposite side of the one-way valve to initiate the reaction. The reaction chamber can further comprise a release agent, such as sodium chloride. The solvent may comprise water. In embodiments, the dry acid reagent is a citric acid powder or an acetic acid powder. The gas produced may be carbon dioxide.

In other variations, the initiating is performed by exposing at least one chemical reagent in the reaction chamber to heat or light. The at least one chemical reagent can be 2,2'-azobisisobutyronitrile. The gas produced can be nitrogen gas.

The reaction chamber may have a volume of at most 1 $cm^3$. The fluid chamber may contain a high-viscosity fluid having an absolute viscosity of from about 5 centipoise to about 1000 centipoise, or a viscosity of at least 40 centipoise.

The piston can be formed from a push surface at the reaction chamber, a stopper, and a rod connecting the push surface and the stopper.

Also described in embodiments herein is a device for delivering a fluid by chemical reaction, comprising: a barrel containing a reagent chamber, a reaction chamber, and a fluid chamber, wherein the reagent chamber is located within a push button member at a top end of the barrel; a plunger separating the reagent chamber from the reaction chamber; a spring biased to push the plunger into the reagent chamber when the push button member is depressed; and a piston separating the reaction chamber from the fluid chamber, wherein the piston moves in response to pressure generated in the reaction chamber.

The push button member can comprise a sidewall closed at an outer end by a contact surface, a lip extending outwards from an inner end of the sidewall, and a sealing member proximate a central portion on an exterior surface of the sidewall.

The barrel may include an interior stop surface that engages the lip of the push button member.

The plunger may comprise a central body having lugs extending radially therefrom, and a sealing member on an inner end which engages a sidewall of the reaction chamber. The interior surface of the push button member can include channels for the lugs.

The reaction chamber may be divided into a mixing chamber and an arm by an interior radial surface, the interior radial surface having an orifice, and the piston being located at the end of the arm. The mixing chamber sometimes includes a gas permeable filter covering the orifice.

The barrel can be formed from a first piece and a second piece, the first piece including the reagent chamber and the reaction chamber, and the second piece including the fluid chamber.

Also disclosed in different embodiments is an injection device for delivering a pharmaceutical fluid to a patient by means of pressure produced by an internal chemical reaction, comprising: a reagent chamber having an activator at an upper end and a one-way valve at a lower end, the one-way valve permitting exit of a reagent from the reagent chamber into a reaction chamber upon activation; the reaction chamber operatively connected to the reagent chamber, having means for receiving the one-way valve at an upper end and a piston at a lower end; and a fluid chamber operatively connected to the reaction chamber, having means for receiving the piston at an upper end, wherein the piston moves in response to pressure generated in the reaction chamber such that the volume of the reaction chamber increases and the volume of the fluid chamber decreases.

BRIEF DESCRIPTION OF THE DRAWINGS

The following is a brief description of the drawings, which are presented for the purposes of illustrating the exemplary embodiments disclosed herein and not for the purposes of limiting the same.

FIG. 1 is a diagram of a chemical reaction that produces a gas for moving a piston within a chamber.

FIG. 9 is a side cross-sectional view of a second exemplary embodiment of an injection device. This embodiment uses a seal to create two separate chambers, and a ring of teeth to break the seal.

FIG. 10 is a cross-sectional perspective view of the engine in the second exemplary embodiment of FIG. 9.

FIG. 11 is a side cross-sectional view of a third exemplary embodiment of an injection device. In this embodiment, pulling the handle upwards (i.e. away from the barrel of the device) breaks the seal between two separate chambers. This figure shows the device prior to pulling the handle upwards.

FIG. 12 is a cross-sectional perspective view of the engine in the third exemplary embodiment of FIG. 11 prior to pulling the handle upwards.

DETAILED DESCRIPTION

Figure 2:
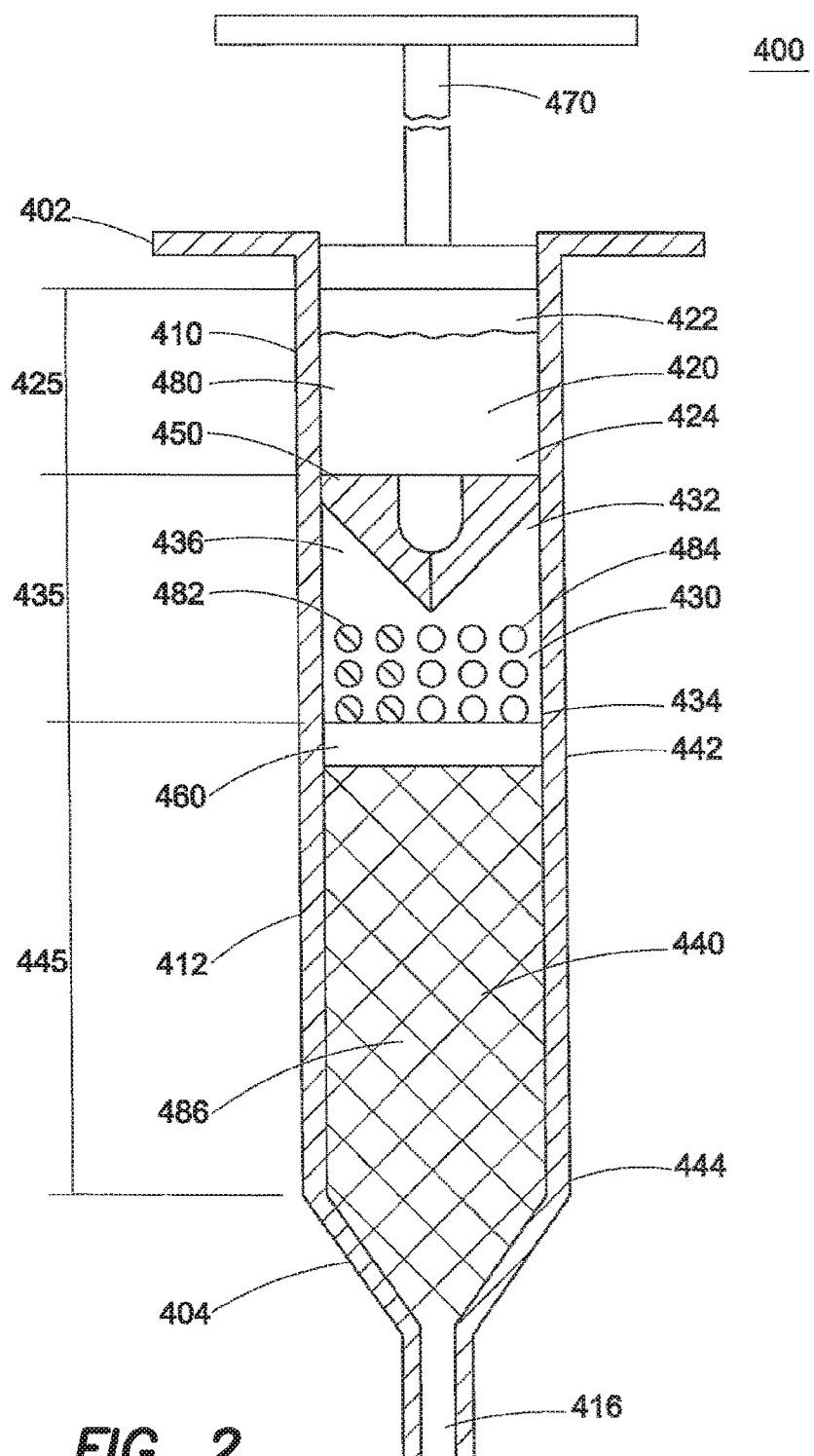
FIG. 2 is a diagram of a first embodiment of a device for delivering a fluid by chemical reaction. The chemical reaction here is generated when two dry chemical reagents are dissolved in a solvent and react. This figure shows the device in a storage state, where the dry reagents are separated from the solvent.

Viscosity can be defined in two ways: "kinematic viscosity" or "absolute viscosity." Kinematic viscosity is a measure of the resistive flow of a fluid under an applied force. The SI unit of kinematic viscosity is $mm^2/sec$, which is 1 centistoke (cSt). Absolute viscosity, sometimes called dynamic or simple viscosity, is the product of kinematic viscosity and fluid density. The SI unit of absolute viscosity is the millipascal-second (mPa-sec) or centipoise (cP), where 1 cP=1 mPa-sec.

A "protein" is a sequence of amino acids that is of sufficient chain length to produce a tertiary or quaternary structure. Examples of proteins include monoclonal antibodies, insulin, human growth hormone, and erythropoietin.

It should be noted that many of the terms used herein are relative terms. For example, the terms "inlet" and "outlet" are relative to a direction of flow, and should not be construed as requiring a particular orientation or location of the structure. Similarly, the terms "upper" and "lower", and "top" and "bottom", are relative to a central point. For example, an upper component is located in one direction from the central point and a lower component would be located in the opposite direction from the central point.

The term "parenteral" refers to a delivery means that is not through the gastrointestinal tract, such as injection or infusion.

The processes of the present disclosure can be used with both manual syringes or auto-injectors and is not limited to cylindrical geometries. The term "syringe" is used interchangeably to refer to manual syringes and auto-injectors of any size or shape. The term "injection device" is used to refer to any device that can be used to inject the fluid into a patient, including for example syringes and patch pumps.

FIG. 1 illustrates the generation of pressure by a chemical reaction for use in delivering a pharmaceutical formulation by injection or infusion. Referring to the left hand side of the figures, one or more chemical reagents 100 are enclosed within a reaction chamber 110. One side of the chamber can move relative to the other sides of the chamber, and acts as a piston 120. The chamber 110 has a first volume prior to the chemical reaction.

A chemical reaction is then initiated within the chamber, as indicated by the "RXN" arrow. A gaseous byproduct 130 is generated at some rate, n(t), where n represents moles of gas produced and t represents time. The pressure is proportional to the amount of gaseous byproduct 130 generated by the chemical reaction, as seen in Equation (1):

$$P\{t\}=[n\{t\}\cdot T]/V \qquad (1)$$

In Equation (1), T represents temperature and V represents the volume of the chamber 110.

The volume of the chamber 110 remains fixed until the additional force generated by the gas pressure on the piston 120 exceeds that needed to push the fluid through a syringe needle. The necessary force depends on the mechanical components present in the system, e.g. frictional forces and mechanical advantages provided by the connector design, the syringe needle diameter, and the viscosity of the fluid. The viscosity of the fluid can be approximated using the Hagen-Poiseuille equation.

Once the minimum pressure required to move the piston 120 is exceeded, the volume of the reaction chamber 110 begins to increases. The movement of the piston 120 causes delivery of fluid within the syringe to begin. The pressure in the chamber 110 depends on both the rate of reaction and the rate of volume expansion, as represented by Equation (1). Preferably, sufficient gas is generated to account for the volume expansion, while not generating too much excess pressure. This can be accomplished by controlling the rates of reaction and gas release in the chamber 110.

The pressure build-up from the chemical-reaction produced gaseous byproduct 130 can be used to push fluid directly adjacent to the piston 120 through the syringe. Pressure build-up may also push fluid in an indirect fashion, e.g., by establishing a mechanical contact between the piston 120 and the fluid, for example by a rod or shaft connecting the piston 120 to a stopper of a prefilled syringe that contains fluid.

The one or more chemical reagents 100 are selected so that upon reaction, a gaseous byproduct 130 is generated. Suitable chemical reagents 100 include reagents that react to generate a gaseous byproduct 130. For example, citric acid ($C_6H_8O_7$) or acetic acid ($C_2H_4O_2$) will react with sodium bicarbonate ($NaHCO_3$) to generate carbon dioxide, $CO_2$, which can be initiated when the two reagents are dissolved in a common solvent, such as water. Alternatively, a single reagent may generate a gas when triggered by an initiator, such as light, heat, or dissolution. For, example, the single reagent 2,2'-azobisisobutyronitrile (AIBN) can be decomposed to generate nitrogen gas ($N_2$) at temperatures of 50° C.-65° C. The chemical reagent(s) are selected so that the chemical reaction can be easily controlled.

One aspect of the present disclosure is the combination of various components to result in (i) enough force to deliver a viscous fluid in a short time period and (ii) in a small package that is compatible with the intended use, i.e. driving a syringe. In time, size, and in force must all come together to achieve the desired injection.

In examples described further herein, an injection device using a gas-generating chemical reaction was used to displace fluid having a viscosity greater than 70 centipoise (cP) through a 27 gauge thin-wall (TW) needle in less than 10 seconds. A 27 gauge thin-wall needle has a nominal outer diameter of 0.016±0.0005 inches, a nominal inner diameter of 0.010±0.001 inches, and a wall thickness of 0.003 inches. Such results are expected to also be obtained with needles having larger nominal inner diameters.

The selection of the chemical reagent(s) can be based on different factors. One factor is the dissolution rate of the reagent, i.e. the rate at which the dry powder form of the reagent dissolves in a liquid. The dissolution rate can be modified by changing the particle size or surface area of the powder, encapsulating the powder with a coating that dissolves first, or changes in the solvent quality. Another factor is the desired pressure versus time profile. The pressure versus time profile can be controlled by modifying the kinetics of the reaction. In the simplest case, the kinetics of a given reaction will depend on factors such as the concentration of the reagents, depending on the "order" of the chemical reaction, and the temperature. For many reagents 100, including those in which two dry reagents must be mixed, the kinetics will depend on the rate of dissolution. For example, by combining powders that have two different dissolution rates, the pressure versus time profile can be modified, enabling constant pressure over time or a profile having a burst in pressure at a specified time. Introduction of a catalyst can be used to the same effect. Alternatively, a delivered volume versus time profile can have a constant slope. The term "constant" refers to the given profile having a linear upward slope over a time period of at least 2 seconds, with an acceptable error of ±15%.

This ability to tune the chemical reaction allows the devices of the present disclosure to accommodate different fluids (with varying volumes and/or viscosities), patient needs, or delivery device designs. Additionally, while the chemical reaction proceeds independently of the geometry of the reaction chamber, the shape of the reaction chamber can affect how accumulated pressure acts on the piston.

The target pressure level for providing drug delivery may be determined by the mechanics of the syringe, the viscosity of the fluid, the diameter of the needle, and the desired delivery time. The target pressure is achieved by selecting the appropriate amount and stoichiometric ratio of reagent, which determines n (moles of gas), along with the appropriate volume of the reaction chamber. The solubility of the gas in any liquid present in the reaction chamber, which will not contribute to the pressure, should also be considered.

If desired, a release agent may be present in the reaction chamber to increase the rate of fluid delivery. When a solvent, such as water, is used to facilitate diffusion and reaction between molecules, the generated gas will have some solubility or stability in the solvent. The release agent facilitates release of any dissolved gas into the head space of the chamber. The release agent decreases the solubility of the gas in the solvent. Exemplary release agents include a nucleating agent that facilitates the nucleation, growth, and release of gas bubbles via heterogeneous nucleation. An exemplary release agent is sodium chloride (NaCl). The presence of the release agent can increase the overall rate of many chemical reactions by increasing the dissolution rate, which is often the rate limiting factor for pressure generation for dry (powder) reagents. The release agent may also be considered to be a catalyst.

In particular embodiments, the volume of the reaction chamber is 1 $cm^3$ or less. The other components of the device can be dimensioned to match the volume of the reaction chamber. A reaction chamber no more than 1 $cm^3$ allows enables chemical-reaction delivery of a high-viscosity fluid with a limited injection space or footprint.

FIG. 2 illustrates one exemplary embodiment of a device (here, a syringe) that can be used to deliver a high-viscosity fluid using a chemical reaction between reagents to generate a gas. The syringe 400 is depicted here in a storage state or a non-depressed state in which the chemical reaction has not yet been initiated. The needle is not included in this illustration.

The syringe 400 includes a barrel 410 that is formed from a sidewall 412, and the interior space is divided into three separate chambers. Beginning at the top end 402 of the barrel, the syringe includes a reagent chamber 420, a reaction chamber 430, and a fluid chamber 440. The plunger 470 is inserted into an upper end 422 of the reagent chamber. A one-way valve 450 is present at a lower end 424 of the reagent chamber, forming a radial surface. The one-way valve 450 is also present at the upper end 432 of the reaction chamber. The one-way valve 450 is directed to permit material to exit the reagent chamber 420 and to enter the reaction chamber 430. The lower end 434 of the reaction chamber is formed by a piston 460. Finally, the piston 460 is present at the upper end 442 of the fluid chamber. The orifice 416 of the barrel is at the lower end 444 of the fluid chamber, and at the bottom end 404 of the syringe. It should be noted that the one-way valve 450 is fixed in place and cannot move within the barrel 410. In contrast, the piston 460 can move within the barrel in response to pressure. Put another way, the reaction chamber 430 is defined by the one-way valve 450, the barrel sidewall 412, and the piston 460.

The reaction chamber 430 can also be described as having a first end and a second end. The moveable piston 460 is at the first end 434 of the reaction chamber, while the one-way valve 450 is present at the second end 432 of the reaction chamber. In this illustration, the reaction chamber 430 is directly on one side of the piston 460, and the fluid chamber 440 is directly on the opposite side of the piston.

The reagent chamber 420 contains at least one chemical reagent, a solvent, and/or a release agent. The reaction chamber 430 contains at least one chemical reagent, a solvent, and/or a release agent. The fluid chamber 440 contains the fluid to be delivered. As depicted here, the reagent chamber 420 contains a solvent 480, the reaction chamber 430 contains two different chemical reagents 482, 484 in a dry powder form, and the fluid chamber 440 contains a high-viscosity fluid 486. Again, it should be noted that this figure is not drawn to scale. The chemical reagents, as illustrated here, do not fill up the entire volume of the reaction chamber. Instead, a head space 436 is present within the reaction chamber.

In specific embodiments, the reagent chamber contains a bicarbonate which has been pre-dissolved in a solvent, and the reaction chamber contains a dry acid powder. It was found that passive mixing of reagents in the solvent was a problem that would reduce the speed of reaction. Bicarbonate was pre-dissolved, otherwise it was too slow to dissolve and participate in the gas generating reaction. In more specific embodiments, potassium bicarbonate was used. It was found that sodium bicarbonate did not react as quickly. Citrate was used as the dry acid powder because it was fast-dissolving and fast-reacting. Sodium chloride (NaCl) was included as a dry release agent with the citrate. The sodium chloride provided nucleation sites to allow the gas to evolve from solution more quickly.

Each chamber has a volume, which in the depicted illustration is proportional to the height of the chamber. The reagent chamber 420 has a height 425, the reaction chamber 430 has a height 435, and the fluid chamber 440 has a height 445. In this non-depressed state, the volume of the reaction chamber is sufficient to contain the solvent and the two chemical reagents.

In particular embodiments, the volume of the reaction chamber is 1 $cm^3$ or less. The other components of the device can be dimensioned to match the volume of the reaction chamber. A reaction chamber no more than 1 $cm^3$ allows enables chemical-reaction delivery of a high-viscosity fluid with a limited injection space or footprint.

Figure 3:
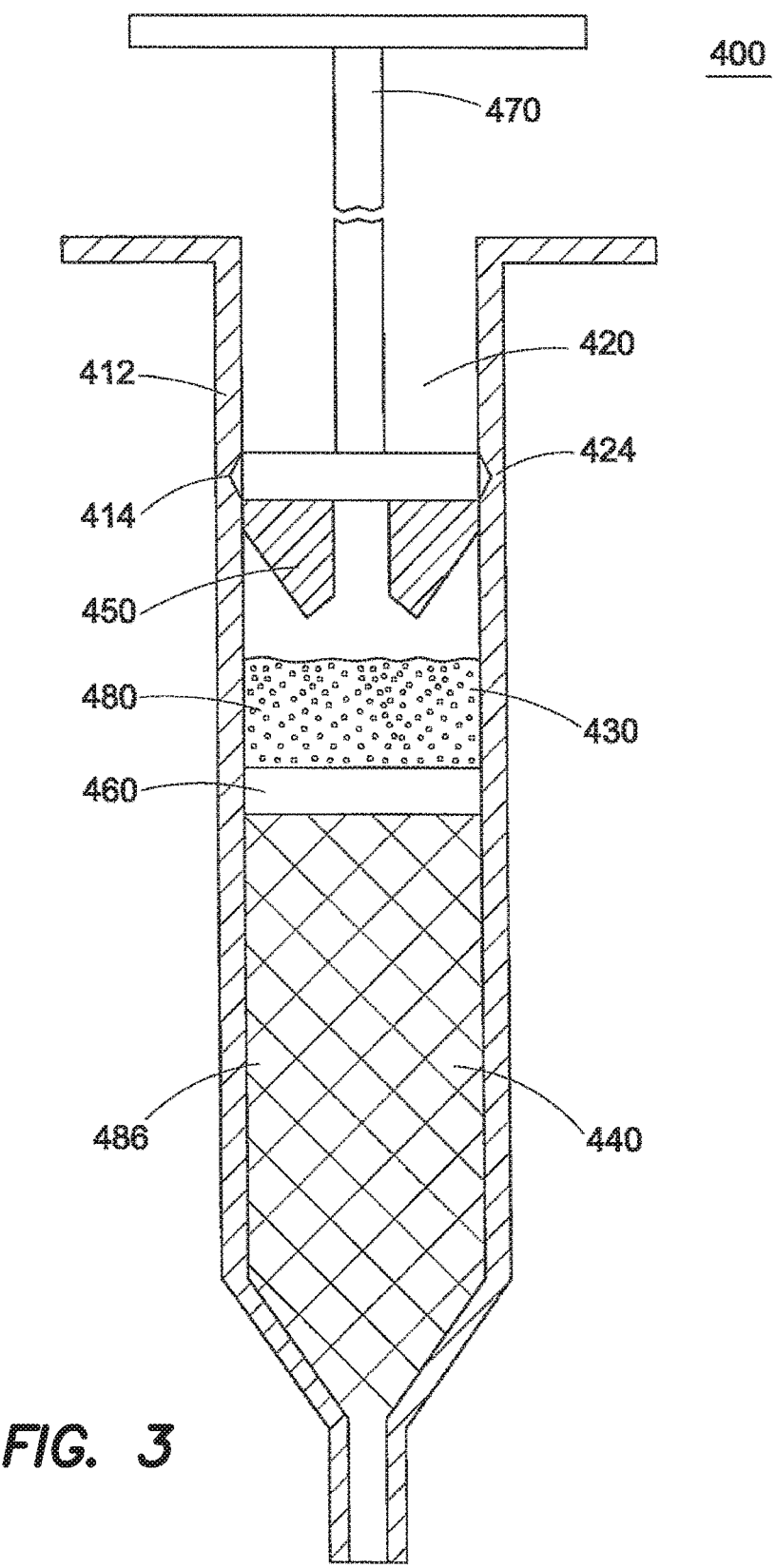
FIG. 3 is a diagram showing the device of FIG. 2 after the dry reagents are combined with the solvent.

In FIG. 3, the plunger 470 has been depressed, i.e. the syringe is in a depressed state. This action causes the one-way valve 450 to be opened, and the solvent 480 enters into the reaction chamber 430 and dissolves the two chemical reagents (illustrated now as bubbles in the solvent). After the plunger 470 is depressed and no further pressure is being exerted on the one-way valve, the one-way valve 450 closes (this figure shows the valve in an open state). In particular embodiments, the barrel sidewall 412 at the lower end 424 of the reagent chamber may contain grooves 414 or is otherwise shaped to capture the plunger 470. Put another way, the plunger 470 cooperates with the lower end 424 of the reagent chamber 420 to lock the plunger in place after being depressed.

Figure 4:
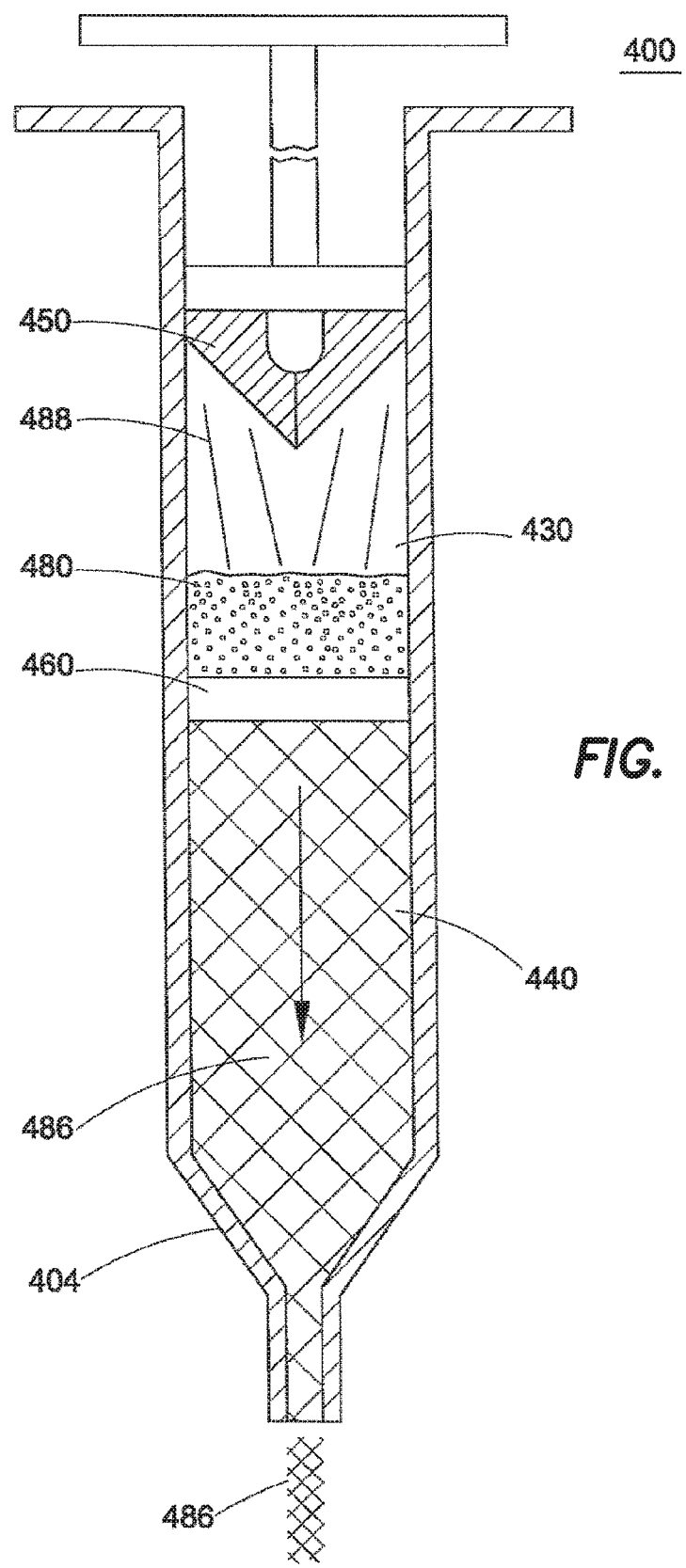
FIG. 4 is diagram showing the device of FIG. 2 with the piston being pushed by gas pressure to deliver the fluid.

In FIG. 4, the dissolution of the two chemical reagents in the solvent has resulted in the generation of a gas 488 as a byproduct of the chemical reaction. As the amount of gas increases, the pressure exerted on the piston 460 increases until, after reaching a threshold value, the piston 460 moves downward towards the bottom end 404 of the syringe (as indicated by the arrow). This causes the volume of the reaction chamber 430 to increase, and the volume of the fluid chamber 440 to decrease. This results in the high-viscosity fluid 486 in the fluid chamber being dispensed through the orifice. Put another way, the combined volume of the reaction chamber 430 and the fluid chamber remains constant, but the volume ratio of reaction chamber to fluid chamber 440 will increase as gas is generated in the reaction chamber. Note that the one-way valve 450 does not permit the gas 488 to escape from the reaction chamber into the reagent chamber.

The syringe can provide consistent force when the following elements are properly controlled: (i) the particle size of the dry powder reagent; (ii) the moisture content of the dry powder reagent; (iii) the mass of the reagents and the quantity of release agent; and (iv) the shape configuration of the chambers for consistent filling and packaging.

Figure 5:
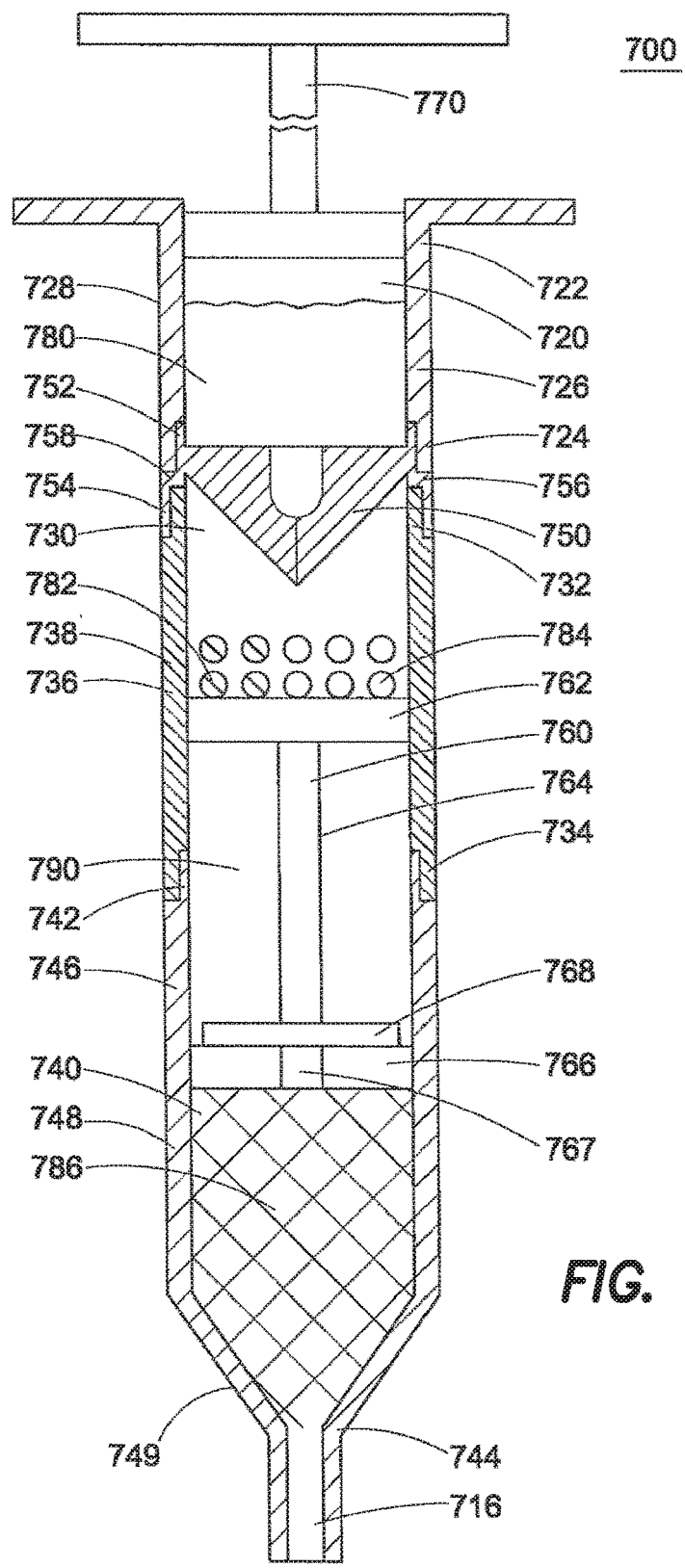
FIG. 5 is a diagram showing another exemplary embodiment of a device for delivering a fluid by chemical reaction of two reagents in a solvent. This device is made in four separate pieces that are joined together to form a combined device similar to that shown in FIG. 2.

FIG. 5 illustrates another variation of a device 700 that uses a chemical reaction between reagents to generate gas. This illustration is in a storage state. Whereas the barrel of FIG. 2 is shown as being made from an integral sidewall, the barrel in the device of FIG. 5 is made of several shorter pieces. This construction can simplify manufacturing and filling of the various chambers of the overall device. Another large difference in this variation is that the piston 760 is made up of three different parts: a push surface 762, a rod 764, and a stopper 766.

Beginning at the top of FIG. 5, the reagent chamber 720 is made from a first piece 726 that has a first sidewall 728 to define the sides of the reagent chamber. The plunger 770 is inserted in the upper end 722 of the piece to seal that end. The first piece 720 can then be turned upside down to fill the reagent chamber 720 with the solvent 780.

A second piece 756 containing the one-way valve 750 can then be joined to the lower end 724 of the first piece to seal the reagent chamber 720. A second sidewall 758 surrounds the one-way valve. The lower end 724 of the first piece and the upper end 752 of the second piece can be joined using known means, such as screw threads (e.g. a Luer lock). As illustrated here, the lower end of the first piece would have internal threads, while the upper end of the second piece would have the external threads.

The third piece 736 is used to form the reaction chamber 730, and is also formed from a third sidewall 738. The push surface 762 of the piston is located within the third sidewall 738. After placing the chemical reagents, solvent, and/or release agent upon the push surface, the lower end 754 of the second piece and the upper end 732 of the third piece are joined together. Two reagents 782, 784 are depicted here. The rod 764 of the piston extends down from the push surface 762.

Finally, the fourth piece 746 is used to form the fluid chamber 740. This fourth piece is formed from a fourth sidewall 748 and a conical wall 749 that tapers to form the orifice 716 from which fluid will be expelled. The orifice is located at the lower end 744 of the fluid chamber. The fluid chamber can be filled with the fluid to be delivered, and the stopper 766 can then be placed in the fluid chamber. As seen here, the stopper 766 may include a vent hole 767 so that air can escape from the fluid chamber as the stopper is being pushed down to the surface of the fluid 786 to prevent air from being trapped in the fluid chamber. A cap 768 attached to the lower end of the piston rod 764 can be used to cover the vent hole 767. Alternatively, the lower end of the piston rod can be inserted into the vent hole. The lower end 734 of the third piece and the upper end 742 of the fourth piece are then joined together.

As previously noted, the piston 760 in this variation is formed from the push surface 762, the rod 764, and the stopper 766 being connected together. An empty volume 790 is thus present between the reaction chamber 730 and the fluid chamber 740. The size of this empty volume can be varied as desired. For example, it may be useful to make the overall device longer so that it can be more easily grasped by the user. Otherwise, this variation operates in the same manner as described above with regards to FIGS. 2-4. The push surface portion of the piston acts in the reaction chamber, and the stopper portion of the piston acts in the fluid chamber. It should also be noted that the push surface, rod, stopper, and optional cap can be one integral piece, or can be separate pieces.

Figure 6:
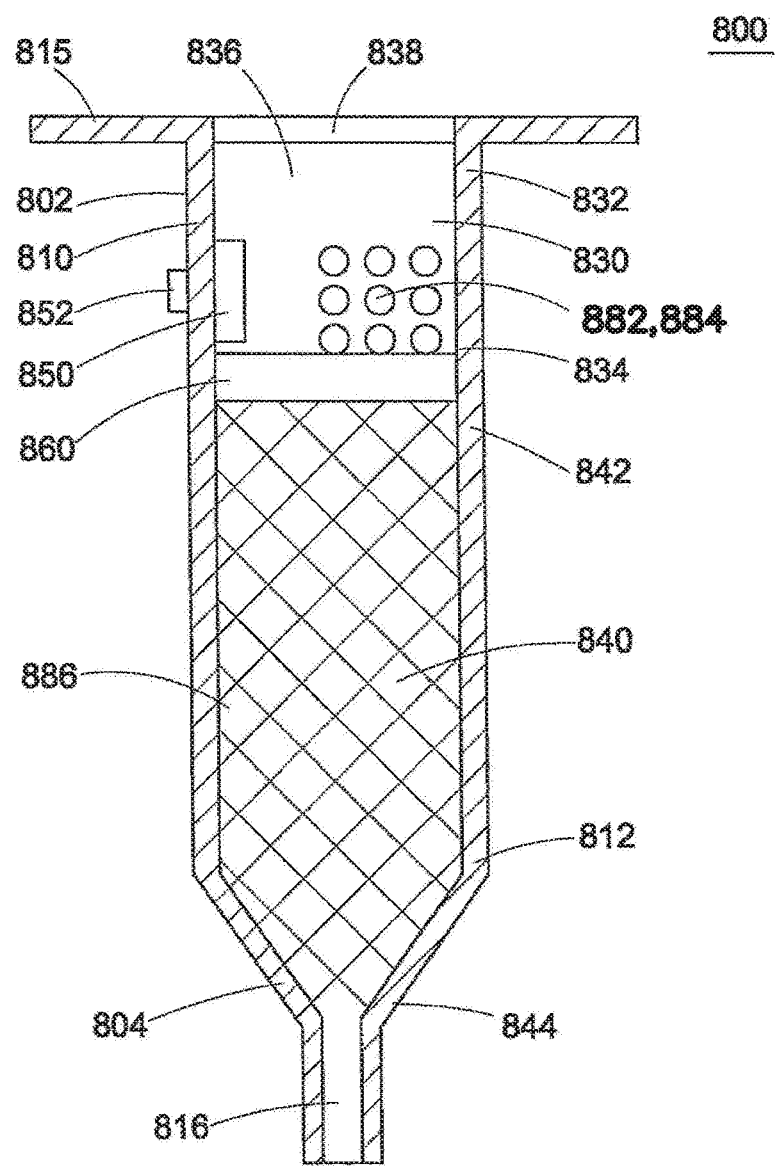
FIG. 6 is a diagram of a first embodiment of a device for delivering a fluid by chemical reaction. The chemical reaction here is generated when a chemical reagent is exposed to heat. The device includes a thermal source.

FIG. 6 illustrates an exemplary embodiment of a device (again, a syringe) that can be used to deliver a high-viscosity fluid using a chemical reaction initiated by heat to generate a gas. Again, the syringe 800 is depicted here in a storage state.

The barrel 810 is formed from a sidewall 812 and the interior space is divided into two separate chambers, a reaction chamber 830 and a fluid chamber 840. The reaction chamber 830 is present at an upper end 802 of the syringe. The upper end 832 of the reaction chamber is formed by a radial wall 838. Located within the reaction chamber is a thermal source 850 that can be used for heating. The thermal source 850 may be located on the radial wall 838 or, as depicted here, on the barrel sidewall 812.

The lower end 834 of the reaction chamber is formed by a piston 860. The reaction chamber 830 is defined by the radial wall 838, the barrel sidewall 812, and the piston 860. The piston 860 is also present at the upper end 842 of the fluid chamber. The orifice 816 of the barrel is at the lower end 844 of the fluid chamber, i.e. at the lower end 804 of the syringe. Again, only the piston 860 portion of the reaction chamber can move within the barrel 810 in response to pressure. The radial wall 838 is fixed in place, and is solid so that gas cannot pass through.

The reaction chamber contains a chemical reagent 882. For example, the chemical reagent can be 2,2'-azobisisobutyronitrile. A head space 836 may be present in the reaction chamber. The fluid chamber 840 contains a fluid 886.

An activation trigger 852 is present on the syringe, which can be for example on top near the finger flange 815 or on the external surface 816 of the barrel sidewall. When activated, the thermal source 850 generates heat. The thermal source can be, for example, an infrared light emitting diode (LED). The chemical reagent 882 is sensitive to heat, and generates a gas (here, $N_2$). The pressure generated by the gas causes the piston 860 to move, expelling the high-viscosity fluid 886 in the fluid chamber 840.

It should be noted again that the piston may alternatively be the push surface, rod, and stopper version described in FIG. 5. This version may be appropriate here as well.

In an alternative embodiment, the thermal source is replaced by a light source 854 which can illuminate the reaction chamber 830. The chemical reagent 884 here is sensitive to light, and generates a gas upon exposure to light. For example, the chemical reagent may be silver chloride (AgCl). The pressure generated by the gas causes the piston to move, expelling the high-viscosity fluid in the fluid chamber. The piston version of FIG. 5 can also be used here if desired.

Any suitable chemical reagent or reagents can be used to generate a gas. For example, bicarbonate will react with acid to form carbon dioxide. Sodium, potassium, and ammonium bicarbonate are examples of suitable bicarbonates. Suitable acids could include acetic acid, citric acid, potassium bitartrate, disodium pyrophosphate, or calcium dihydrogen phosphate. Any gas can be generated by the chemical reaction, such as carbon dioxide, nitrogen gas, oxygen gas, chlorine gas, etc. Desirably, the generated gas is inert and non-flammable. Metal carbonates, such as copper carbonate or calcium carbonate, can be decomposed thermally to produce $CO_2$ and the corresponding metal oxide. As another example, 2,2'-azobisisobutyronitrile (AIBN) can be heated to generate nitrogen gas. As yet another example, the reaction of certain enzymes (e.g. yeast) with sugar produces CO2. Some substances readily sublime, going from solid to gas. Such substances include but are not limited to naphthalene and iodine. Hydrogen peroxide can be decomposed with catalysts such as enzymes (e.g. catalase) or manganese dioxide to produce oxygen gas. As another example, silver chloride will decompose upon exposure to light.

It is contemplated that the high-viscosity fluid to be dispensed using the devices of the present disclosure can be a solution, dispersion, suspension, emulsion, etc. The high-viscosity formulation may contain a protein, such as a monoclonal antibody or some other protein which is therapeutically useful. The protein may have a concentration of from about 150 mg/ml to about 500 mg/ml. The high-viscosity fluid may have an absolute viscosity of from about 5 centipoise to about 1000 centipoise. In other embodiments, the high-viscosity fluid has an absolute viscosity of at least 40 centipoise, or at least 60 centipoise. The high-viscosity fluid may further contain a solvent or non-solvent, such as water, perfluoroalkane solvent, safflower oil, or benzyl benzoate.

Figure 7:
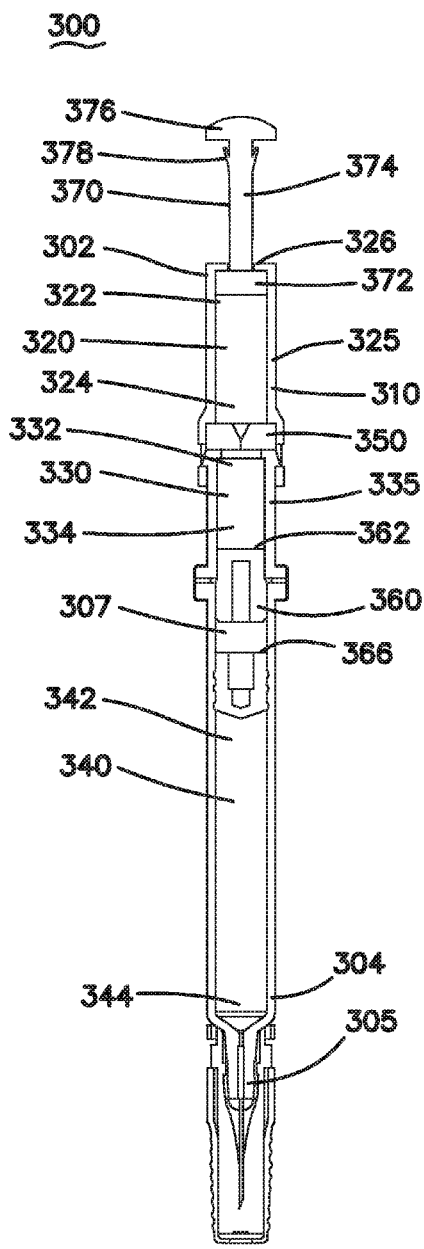
FIG. 7 is a side cross-sectional view of a first exemplary embodiment of an injection device. This embodiment uses a one-way valve to create two separate chambers.
Figure 8:
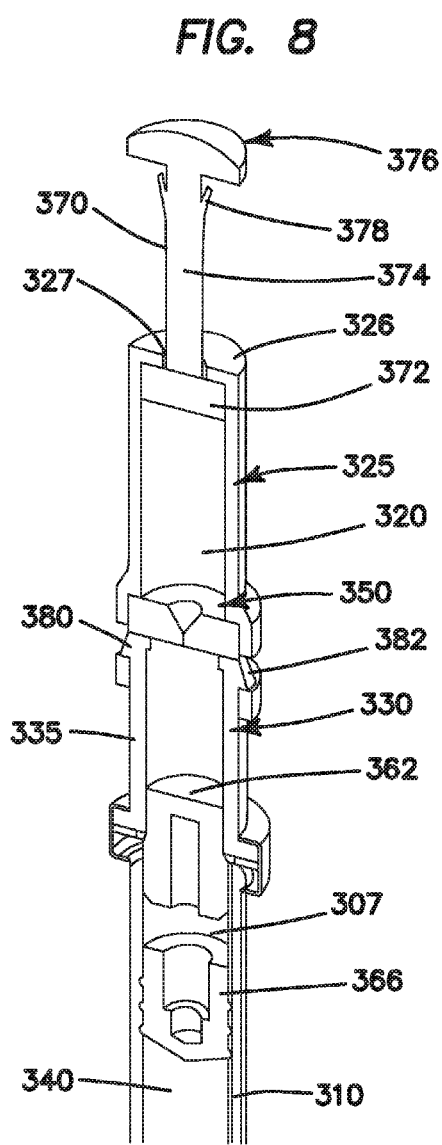
FIG. 8 is a cross-sectional perspective view of the engine in an exemplary embodiment of FIG. 7.

FIG. 7 and FIG. 8 are different views of the first exemplary embodiment of an injection device (here, a syringe) that can be used to deliver a high-viscosity fluid using a chemical reaction between reagents to generate a gas. The syringe 300 is depicted here in a storage state or a non-depressed state in which the chemical reaction has not yet been initiated. FIG. 7 is a side cross-sectional view, and FIG. 8 is a perspective view of the engine of the syringe.

The syringe 300 includes a barrel 310 whose interior space is divided into three separate chambers. Beginning at the top end 302 of the barrel, the syringe includes an upper chamber 320, a lower chamber 330, and a fluid chamber 340. These three chambers are coaxial, and are depicted here as having a cylindrical shape. The lower chamber may also be considered a reaction chamber.

The plunger 370 is inserted into an upper end 322 of the upper chamber, and the stopper 372 of the plunger travels through only the upper chamber. A one-way valve 350 is present at a lower end 324 of the upper chamber, forming a radial surface. The one-way valve 350 is also present at the upper end 332 of the lower chamber. The one-way valve 350 is directed to permit material to exit the upper chamber 320 and to enter the lower chamber 330. A piston 360 is present at the lower end 334 of the lower chamber. The piston 360 is also present at the upper end 342 of the fluid chamber. As illustrated here, the piston is formed of at least two pieces, a push surface 362 that is at the lower end of the lower chamber and a head 366 at the upper end of the fluid chamber. The needle 305 is at the lower end 344 of the fluid chamber, and at the bottom end 304 of the syringe. It should be noted that the one-way valve 350 is fixed in place and cannot move within the barrel 310, or in other words is stationary relative to the barrel. In contrast, the piston 360 can move within the barrel in response to pressure. Put another way, the lower chamber 330 is defined by the one-way valve 350, the continuous sidewall 312 of the barrel, and the piston 360.

The lower chamber 330 can also be described as having a first end and a second end. The moveable piston 360 is at the first end 334 of the lower chamber, while the one-way valve 350 is present at the second end 332 of the lower chamber. In this illustration, the lower chamber 330 is directly on one side of the piston 360, and the fluid chamber 340 is directly on the opposite side of the piston.

As previously noted, the piston 360 is formed from at least the push surface 362 and the head 366. These two pieces can be connected together physically, for example with a rod (not shown) that has the push surface and the head on opposite ends. Alternatively, it is also contemplated that an incompressible gas could be located between the push surface and the head. An empty volume 307 would thus be present between the lower chamber 330 and the fluid chamber 340. The size of this empty volume could be varied as desired. For example, it may be useful to make the overall device longer so that it can be more easily grasped by the user. Alternately, as illustrated in another embodiment in FIG. 9 and FIG. 10 further herein, the piston may use a balloon that acts as the push surface and acts upon the head 366. As yet another variation, the piston may be a single piece, with the push surface being on one side of the single piece and the head being on the other side of the single piece.

The upper chamber 320 contains at least one chemical reagent or a solvent. The lower chamber 330 contains at least one chemical reagent or a solvent. The fluid chamber 340 contains the fluid to be delivered. It is generally contemplated that dry reagents will be placed in the lower chamber, and a wet reagent (i.e. solvent) will be placed in the upper chamber. As depicted here, the upper chamber 320 would contain a solvent, the lower chamber 330 would contain two different chemical reagents in a dry powder form, and the fluid chamber 340 would contain a high-viscosity fluid. The reagent(s) in either chamber may be encapsulated for easier handling during manufacturing. Each chamber has a volume, which in the depicted illustration is proportional to the height of the chamber. In this non-depressed state, the volume of the lower chamber is sufficient to contain the solvent and the two chemical reagents.

When the plunger in the syringe of FIG. 7 and FIG. 8 is depressed, the additional pressure causes the one-way valve 350 to open, and the solvent in the upper chamber 320 enters into the lower chamber 330 and dissolves the two chemical reagents. After the plunger 370 is sufficiently depressed and no further pressure is being exerted on the one-way valve, the one-way valve 350 closes. As illustrated here, the plunger includes a thumbrest 376 and a pressure lock 378 on the shaft 374 which is proximate to the thumbrest. The pressure lock cooperates with an upper surface 326 of the upper chamber to lock the plunger in place. The two chemical reagents may react with each other in the solvent to generate gas in the lower chamber. As the amount of gas increases, the pressure exerted on the push surface 362 of the piston 360 increases until, after reaching a threshold value, the piston 360 moves downward towards the bottom end 304 of the syringe. This causes the volume of the lower chamber 330 to increase, and the volume of the fluid chamber 340 to decrease. This results in the high-viscosity fluid in the fluid chamber being dispensed through the orifice (by the head 366). Put another way, the combined volume of the lower chamber 330 and the fluid chamber remains constant, but the volume ratio of lower chamber to fluid chamber 340 will increase as gas is generated in the reaction chamber. Note that the one-way valve 350 does not permit the gas to escape from the lower chamber into the upper chamber. Also, the pressure lock 378 on the plunger permits the stopper 372 to act as a secondary backup to the one-way valve 350, and also prevents the plunger from being pushed up and out of the upper chamber.

In specific embodiments, the upper chamber contains a bicarbonate which has been pre-dissolved in a solvent, and the lower chamber contains a dry acid powder. It was found that passive mixing of reagents in the solvent was a problem that would reduce the speed of reaction. Bicarbonate was pre-dissolved, otherwise it was too slow to dissolve and participate in the gas generating reaction. In more specific embodiments, potassium bicarbonate was used. It was found that sodium bicarbonate did not react as quickly. Citrate was used as the dry acid powder because it was fast-dissolving and fast-reacting. Sodium chloride (NaCl) was included as a dry release agent with the citrate. The sodium chloride provided nucleation sites to allow the gas to evolve from solution more quickly.

It should be noted that the upper chamber 320, the lower chamber 330, and the fluid chamber 340 are depicted here as being made from separate pieces that are joined together to form the syringe 300. The pieces can be joined together using methods known in the art. For example, the upper chamber is depicted here as being formed from a sidewall 325 having a closed upper end 322 with a port 327 for the plunger. The stopper 372 of the plunger is connected to the shaft 374. The one-way valve 350 is a separate piece which is inserted into the open lower end 324 of the upper chamber. The lower chamber is depicted here as being formed from a sidewall 335 having an open upper end 332 and an open lower end 334. The upper end of the lower chamber and the lower end of the upper chamber cooperate to lock together and fix the one-way valve in place. Here, the locking mechanism is a snap fit arrangement, with the upper end of the lower chamber having the cantilever snap 380 that includes an angled surface and a stop surface. The lower end of the upper chamber has the latch 382 that engages the cantilever snap. Similarly, the lower chamber and the fluid chamber are fitted together with a ring-shaped seal.

FIG. 9 and FIG. 10 are different views of an exemplary embodiment of an injection device of the present disclosure. The syringe 500 is depicted here in a storage state or a non-depressed state in which the chemical reaction has not yet been initiated. FIG. 9 is a side cross-sectional view, and FIG. 10 is a perspective view of the engine of the syringe.

Again, the syringe includes a barrel 510 whose interior space is divided into three separate chambers. Beginning at the top end 502 of the barrel, the syringe includes an upper chamber 520, a lower chamber 530, and a fluid chamber 540. These three chambers are coaxial, and are depicted here as having a cylindrical shape. The lower chamber 530 may also be considered a reaction chamber.

In this embodiment, the upper chamber 520 is a separate piece located within the barrel 510. The barrel is illustrated here as an outer sidewall 512 that surrounds the upper chamber. The upper chamber 520 is illustrated here with an inner sidewall 525 and a top wall 527. A shaft 574 and a thumbrest I button 576 extend from the top wall 527 of the upper chamber in the direction away from the barrel. Thus, the upper chamber 520 could also be considered as forming the lower end of a plunger 570. The lower end 524 of the upper chamber is closed off with a seal 528, i.e. a membrane or barrier such that the upper chamber has an enclosed volume. It should be noted that the inner sidewall 525 of the upper chamber travels freely within the outer sidewall 512 of the barrel. The upper chamber moves axially relative to the lower chamber.

The lower chamber 530 has a port 537 at its upper end 532. A ring 580 of teeth is also present at the upper end 532. Here, the teeth surround the port. Each tooth 582 is illustrated here as having a triangular shape, with a vertex oriented towards the seal 528 of the upper chamber, and each tooth is angled inwards towards the axis of the syringe. The term "tooth" is used here generally to refer to any shape that can puncture the seal of the upper chamber.

A piston 560 is present at the lower end 534 of the lower chamber 530. The piston 560 is also present at the upper end 542 of the fluid chamber 540. Here, the piston 560 includes the head 566 and a balloon 568 within the lower chamber that communicates with the port 537 in the upper end. Put another way, the balloon acts as a push surface for moving the head. The head 566 may be described as being below or downstream of the balloon 568, or alternatively the balloon 568 can be described as being located between the head 566 and the port 537. The needle 505 is at the lower end 544 of the fluid chamber, and at the bottom end 504 of the syringe. The balloon is made from a suitably non-reactive material.

The top end 502 of the barrel (i.e. the sidewall) includes a pressure lock 518 that cooperates with the top surface 526 of the upper chamber to lock the upper chamber 520 in place when moved sufficiently towards the lower chamber 530. The upper chamber 520 is illustrated here extending out of the outer sidewall 512. The top end 526 of the outer sidewall is shaped to act as the cantilever snap, and the top surface 526 of the upper chamber acts as the latch.

Alternatively, the top end of the device may be formed as depicted in FIG. 8, with the pressure lock on the shaft proximate to the thumbrest and cooperating with the top end of the device.

As previously described, it is generally contemplated that dry reagents will be placed in the lower chamber 530, and a wet reagent (i.e. solvent) will be placed in the upper chamber 520. Again, the reagent(s) in either chamber may be encapsulated for easier handling during manufacturing. More specifically, it is contemplated that the reagents in the lower chamber would be located within the balloon 568.

During operation of the syringe of FIG. 9 and FIG. 10, pushing the button 576 downwards causes the upper chamber 520 to move into the barrel towards the ring 580 of teeth. The pressure of the upper chamber against the ring of teeth causes the seal 528 to break, releasing the contents of the upper chamber into the lower chamber 530. Here, it is contemplated that the gas-generating reaction occurs within the balloon 568. The increased gas pressure causes the balloon to inflate (i.e. lengthen). This pushes the head 566 towards the bottom end 504 of the syringe (note the upper chamber will not be pushed out of the barrel due to the pressure lock). This again causes the volume of the lower chamber 530 to increase, and the volume of the fluid chamber 540 to decrease. i.e. the volume ratio of lower chamber to fluid chamber to increase.

There is an empty volume 507 present between the balloon 568 and the head 566. An incompressible gas could be located in this empty volume. The size of this empty volume can be varied as desired, for example to make the overall device longer.

Again, the upper chamber 520, the lower chamber 530, and the fluid chamber 540 can be made from separate pieces that are joined together to form the syringe. It should be noted that FIG. 10 is made from five pieces (590, 592, 594, 596, and 598), with the additional pieces being due to the addition of the balloon in the lower chamber and to the upper chamber being separate from the outer sidewall. However, this embodiment could still be made from fewer pieces as in FIG. 8. For example, the balloon could be located close to the ring of teeth.

Figure 13:
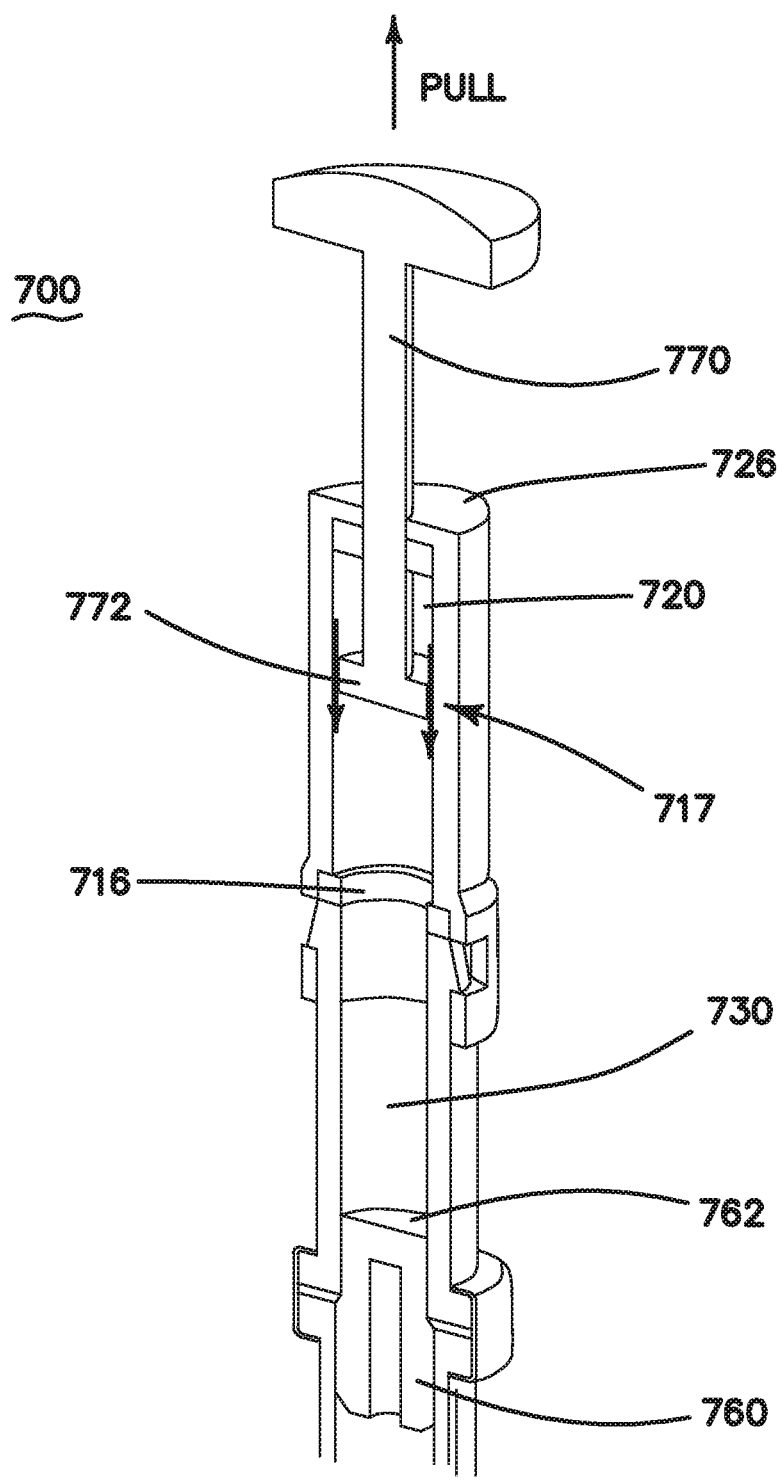
FIG. 13 is a cross-sectional perspective view of the engine in the third exemplary embodiment of FIG. 11 after pulling the handle upwards.

FIG. 11, FIG. 12, and FIG. 13 are different views of a third exemplary embodiment of an injection device of the present disclosure. In this embodiment, the mixing of the chemical reagents is initiated by pulling the plunger handle away from the barrel, rather than towards the barrel as in the embodiments of FIGS. 7-10. FIG. 11 is a side cross-sectional view of the syringe in a storage state. FIG. 12 is a perspective view of the engine of the syringe in a storage state. FIG. 13 is a perspective view of the engine of the syringe in its operating state, i.e. when the handle is pulled upwards away from the barrel of the syringe.

The syringe 700' includes a barrel 710' whose interior space is divided into three separate chambers. Beginning at the top end 702' of the barrel, the syringe includes an upper chamber 720', a lower chamber 730', and a fluid chamber 740'. These three chambers are coaxial, and are depicted here as having a cylindrical shape. The lower chamber may also be considered a reaction chamber.

In this embodiment, the plunger 770' is inserted into an upper end 722' of the upper chamber. In the storage state, the shaft 774' runs through the upper chamber from the lower end 724' to the upper end 722' and through the upper surface 726' of the upper chamber. A seal 728' is present at the top end where the shaft exits the upper chamber. The thumbrest 776' at the upper end of the shaft is outside of the upper chamber. The stopper 772' at the lower end of the shaft cooperates with a seat 716' within the barrel such that the upper chamber has an enclosed volume. For example, the top surface of the stopper may have a larger diameter than the bottom surface of the stopper. The seat 716' may be considered as being at the lower end 724' of the upper chamber, and also as being at the upper end 732' of the lower chamber.

A piston 760' is present at the lower end 734' of the lower chamber. The piston 760' is also present at the upper end 742' of the fluid chamber 740'. As illustrated here, the piston 760' is formed of at least two pieces, a push surface 762' and a head 766'. An empty volume 707' can be present. Other aspects of this piston are similar to that described in FIG. 8. Again, the piston can move within the barrel in response to pressure. The lower chamber 730' can also be described as being defined by the seat 716, the continuous sidewall 712' of the barrel, and the piston 760'. The needle 705' is at the lower end 744' of the fluid chamber, and at the bottom end 704' of the syringe.

During operation of the syringe of FIGS. 11-13, it is generally contemplated that dry reagents will be placed in the lower chamber 730', and a wet reagent (i.e. solvent) will be placed in the upper chamber 720', as previously described. Referring now to FIG. 11, pulling the plunger 770' upwards (i.e. away from the barrel) causes the stopper 772' to separate from the seat 716'. This creates fluid communication between the upper chamber 720' and the lower chamber 730'. The reagent in the upper chamber travels around the stopper into the lower chamber (reference number 717'). The gas-generating reaction then occurs in the lower chamber 730'. The gas pressure pushes the piston 760' towards the bottom end 704' of the syringe. In other words, the volume of the lower chamber increases, and the volume of the fluid chamber decreases. i.e. the volume ratio of lower chamber to fluid chamber increases. One additional advantage to this embodiment is that once the reagents begin generating gas, the pressure created will continue to push the plunger 710' further out of the upper chamber, helping to push more reagent out of the upper chamber 720' into the lower chamber 730', furthering the generation of gas.

Referring to FIG. 12, the barrel 710' is depicted as being made up of three different pieces 790', 792', 794'. A seal 738' is also located between the pieces that make up the lower chamber and the fluid chamber.

Figure 14:
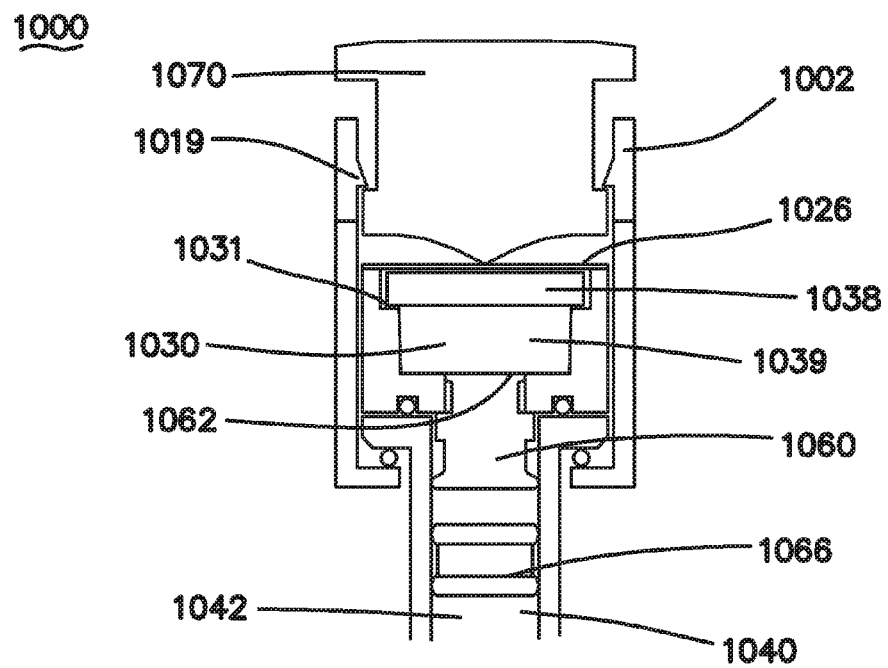
FIG. 14 is a side cross-sectional view of an exemplary embodiment showing the engine using an encapsulated reagent. This figure shows the device in a storage state.
Figure 15:
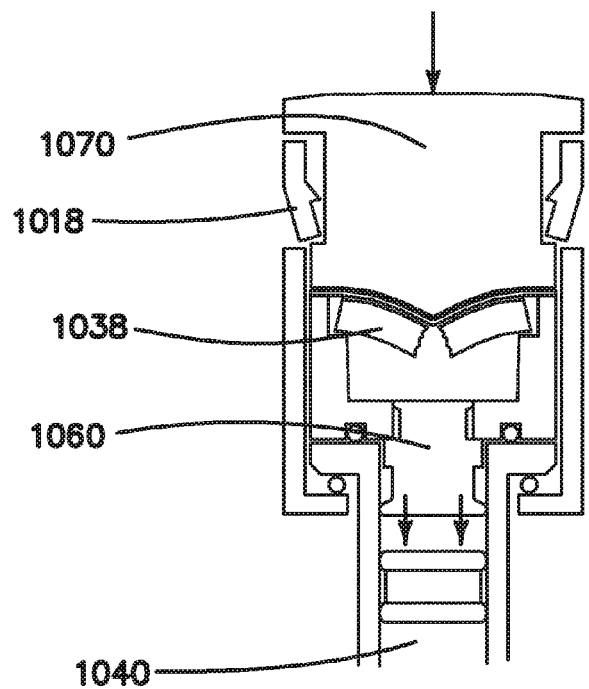
FIG. 15 is a side cross-sectional view of the exemplary embodiment showing the engine using an encapsulated reagent. This figure shows the device in a use state.

FIG. 14 and FIG. 15 are cross-sectional views of one aspect of another exemplary embodiment of the injection device of the present disclosure. In this embodiment, the liquid reagent (i.e. the solvent) is encapsulated in a capsule is broken when a button is pressed. FIG. 14 shows this engine before the button is pressed. FIG. 15 shows the engine after the button is pressed.

Referring first to FIG. 14, the top end 1002 of the syringe 1000 is shown. A reaction chamber 1030 contains a capsule 1038 and dry reagent(s) 1039. Here, the capsule rests on a ledge 1031 above the dry reagent(s). A push surface 1062 of a piston 1060 is present at the lower end of the reaction chamber. The head 1066 of the piston is also visible, and is at the upper end 1042 of the fluid chamber 1040. A button/plunger 1070 is located above the capsule. A seal 1026 may be present between the button 1070 and the capsule 1038. The barrel contains a safety snap 1019 to prevent the button from falling out of the end of the barrel.

If desired, the portion of the reaction chamber containing the capsule could be considered an upper chamber, and the portion of the reaction chamber containing the dry reagent(s) could be considered a lower chamber.

Referring now to FIG. 15, when the button 1070 is pushed, the capsule 1038 is broken, causing the solvent and the dry reagent(s) to mix. This generates a gas that pushes the piston 1060 downward and ejects fluid from the fluid chamber 1040. Pushing the button subsequently engages a pressure lock 1018 that prevents the button from being pushed upwards by the gas pressure.

The embodiments of the figures described above have been illustrated as auto-injectors. Auto-injectors are typically held in the user's hand, have a cylindrical form factor, and have a relatively quick injection time of one second to 30 seconds. It should be noted that the concepts embodied in the above-described figures could also be applied to other types of injection devices, such as patch pumps. Generally, a patch pump has a flatter form factor compared to a syringe, and also has the delivery time is typically greater than 30 seconds. Advantages to using a chemical gas-generating reaction in a patch pump include the small volume required, flexibility in the form/shape, and the ability to control the delivery rate.

Figure 16:
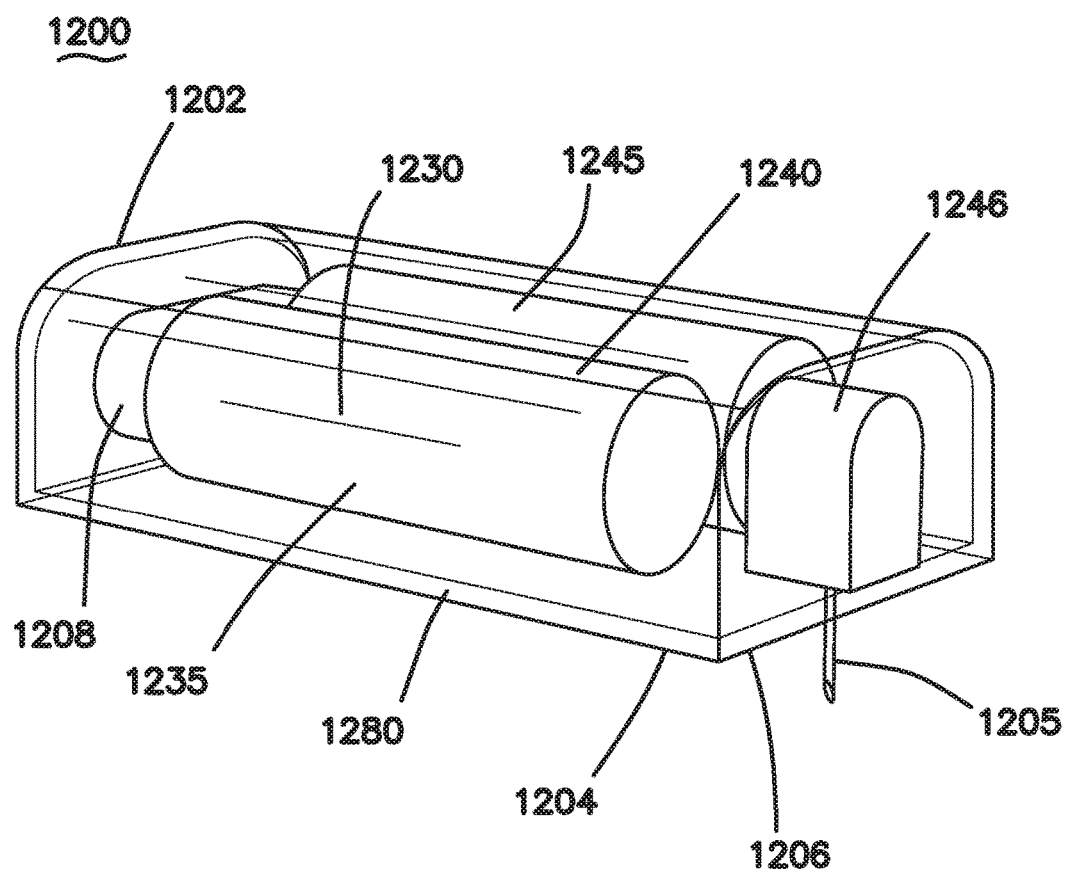
FIG. 16 is a perspective see-through view of a first exemplary embodiment of a patch pump that uses a chemical reaction to inject fluid. Here, the engine and the fluid chamber are side-by-side, and both have rigid sidewalls.

FIG. 16 is an illustration of a typical patch pump 1200. The patch pump includes a reaction chamber 1230 and a fluid chamber 1240 located within a housing 1280. As shown here, the reaction chamber and the fluid chamber are located side-by-side, though this can vary as desired. The reaction chamber 1230 is formed from a sidewall 1235. The fluid chamber 1240 is also formed from a sidewall 1245. The reaction chamber and the fluid chamber are fluidly connected by a passage 1208 at a first end 1202 of the device. The fluid chamber 1240 includes an outlet 1246 that is connected to a needle 1205 located at opposite second end 1204 of the housing. The needle 1205 extends from the bottom 1206 of the housing.

The reaction chamber is divided into a first compartment and a second compartment by a barrier (not visible). In this regard, the first compartment is analogous to the lower chamber, and the second chamber is analogous to the upper chamber previously described.

The reaction chamber can be considered as an engine that causes fluid in the fluid chamber to be ejected. In this regard, it is contemplated that a gas-generating chemical reaction can be initiated by breaking the seal between the first compartment and the second compartment. The barrier could be broken, for example, by bending or snapping the patch pump housing, or by pushing at a designated location on the housing. This causes the reagents to mix. Because the desired delivery time is longer, the speed at which the chemicals are mixed is not as great a concern. The pressure builds up and can act on a piston (not visible) in the fluid chamber, causing fluid to exit through the outlet. It is contemplated that the volume of the reaction chamber and the fluid chamber do not change significantly in this embodiment.

Figure 17:
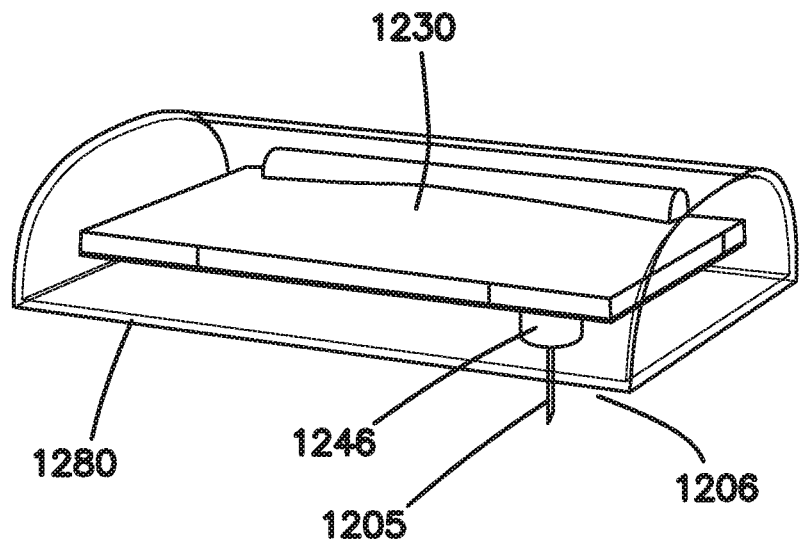
FIG. 17 is a perspective see-through view of a second exemplary embodiment of a patch pump that uses a chemical reaction to inject fluid. Here, the engine is on top of the fluid chamber, and both have a flexible wall. The engine expands and presses the fluid chamber. This figure shows the patch pump when the fluid chamber is empty and prior to use.
Figure 18:
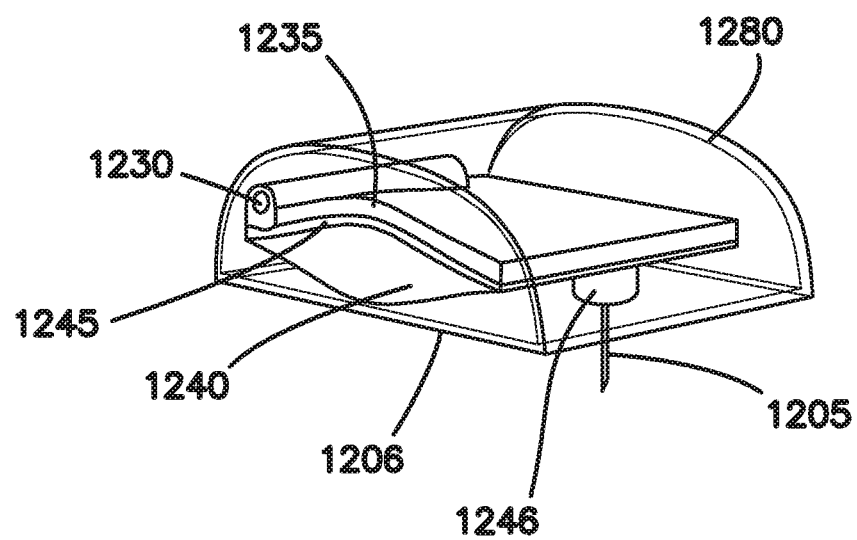
FIG. 18 is a perspective see-through view of the patch pump of FIG. 17, where the fluid chamber is filled.

FIG. 17 and FIG. 18 are perspective see-through views of another exemplary embodiment of a patch pump. In this embodiment, the reaction chamber/engine 1230 is located on top of the fluid chamber 1240. The needle 1205 extends from the bottom 1206 of the housing 1280. In this embodiment, the reaction chamber 1230 includes a flexible wall 1235. The fluid chamber 1240 also includes a flexible sidewall 1245. The flexible wall of the reaction chamber is proximate to the flexible sidewall of the fluid chamber. The reaction chamber and the fluid chamber are not fluidly connected to each other in this embodiment. Instead, it is contemplated that as gas is generated in the reaction chamber, the reaction chamber will expand in volume. The flexible wall 1235 of the reaction chamber will compress the flexible sidewall 1245 of the fluid chamber, causing fluid in the fluid chamber to exit through the outlet 1246. Put another way, the volume ratio of reaction chamber to fluid chamber increases over time as the reaction chamber inflates and the fluid chamber dispenses fluid. It should be noted that a relatively constant volume is required in this embodiment, so that the increasing volume of the reaction chamber causes compression of the fluid chamber. This can be accomplished, for example, by including a rigid backing on the opposite side of the reaction chamber from the flexible wall, or by making the housing from a relatively rigid material.

Figure 19:
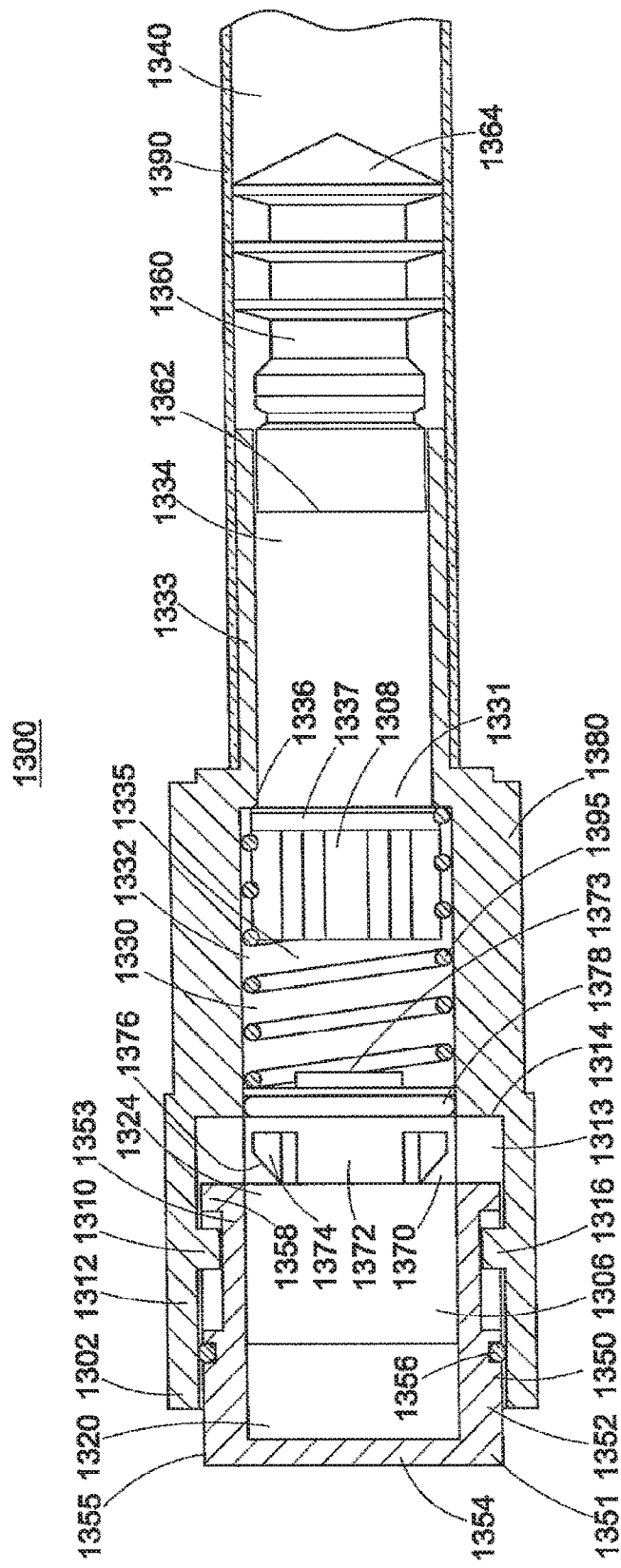
FIG. 19 is a side cross-sectional view of another exemplary embodiment of a syringe that uses a gas-generating chemical reaction. Here, a stopper is biased by a compression spring to travel through the reagent chamber and ensure its contents are emptied into the reaction chamber.

FIG. 19 illustrates another exemplary embodiment of a device (here, a syringe) that can be used to deliver a high-viscosity fluid using a chemical reaction between reagents to generate a gas. The syringe 1300 is depicted here in a storage state or a non-depressed state in which the chemical reaction has not yet been initiated. The needle is not included in this illustration.

The syringe 1300 includes a barrel 1310 whose interior space is divided into three separate chambers. Beginning at the top end 1302 of the barrel, the syringe includes a reagent chamber 1320, a reaction chamber 1330, and a fluid chamber 1340. These three chambers are coaxial, and are depicted here as having a cylindrical shape. In this embodiment, the barrel of the syringe is formed from two different pieces. The first piece 1380 includes a sidewall 1312 that forms the reaction chamber and provides a space 1313 for the reagent chamber. The sidewall is open at the top end 1302 for a push button described further herein. The fluid chamber is made from a second piece 1390 which can be attached to the first piece.

The sidewall 1312 of the first piece includes an interior radial surface 1314 that divides the first piece into an upper space 1313 and the reaction chamber 1330. The reaction chamber has a smaller inner diameter 1325 compared to the inner diameter 1315 of the upper space.

The reagent chamber is located in a separate push button member 1350 that is located within the upper space 1313 of the first piece and extends through the top end 1302 of the barrel. As illustrated here, the push button member is formed from a sidewall 1352 which is closed at the outer end 1351 by a contact surface 1354, and which forms an interior volume into which reagent is placed (i.e. the reagent chamber). A sealing member 1356 (shown here as an O-ring) is proximate a central portion on the exterior surface 1355 of the sidewall, and engages the sidewall 1312 in the upper space. The inner end 1353 of the sidewall includes a lip 1358 extending outwards from the sidewall. The lip engages an interior stop surface 1316 on the barrel. The reagent chamber is depicted as containing a solvent 1306 in which bicarbonate is dissolved.

A plunger 1370 is located between the reagent chamber 1320 and the reaction chamber 1330. The plunger 1370 is located at the inner end 1324 of the reagent chamber. The plunger includes a central body 1372 having lugs 1374 extending radially therefrom (here shown as four lugs, though the number can vary). The lugs also engage the lip 1358 of the push button member when the syringe is in its storage state. The lugs are shaped with an angular surface 1376, such that the plunger 1370 rotates when the push button member 1350 is depressed. An inner end 1373 of the central body includes a sealing member 1378 (shown here as an O-ring) which engages the sidewall in the reaction chamber.

The reaction chamber 1330 includes a top end 1332 and a bottom end 1334. Another interior radial surface 1336 is located at a central location in the reaction chamber, separating the reaction chamber into a mixing chamber 1335 and an arm/fitting 1333, with the mixing chamber 1335 being proximate the reagent chamber 1320 or the top end 1332. An orifice 1331 within the interior radial surface leads to the arm fitting 1333 which engages the second piece 1390 containing the fluid chamber 1340. The piston 1360 is located at the bottom end of the reaction chamber, i.e. at the end of the arm 1333. Located within the reaction chamber is a dry reagent 1308. Here, the dry reagent is citrate, and is in the form of a tablet. The dry reagent is depicted here as being located upon the interior radial surface, i.e. in the mixing chamber. A gas-permeable I liquid-solid impermeable filter 1337 may be present across the orifice. The filter keeps any dry solid reagent and a liquid inside the mixing chamber to improve mixing.

In addition, a compression spring 1395 is located within the mixing chamber, extending from the interior radial surface 1336 to the inner end 1373 of the plunger. A compression spring stores energy when compressed (i.e. is longer when no load is applied to it). Because the push button member 1350 and the plunger 1370 are fixed in place, the compression spring 1395 is compressed in the storage state. It should be noted that here, the spring surrounds the dry reagent. It is also contemplated, in alternate embodiments, that the dry reagent is attached to the inner end 1373 of the plunger.

Finally, the piston 1360 is also present at the upper end 1342 of the fluid chamber. Again, the piston 1360 can move within the barrel in response to pressure generated in the reaction chamber. The piston can also be described as having a push surface 1362 and a stopper 1364.

The sealing member 1378 of the plunger separates the liquid reagent in the reagent chamber 1320 from the dry reagent in the reaction chamber 1330. While liquid 1306 is illustrated as being present in the push button member, it is also possible that liquid is present in the barrel in the upper space 1313 around the plunger.

When the push button member 1350 is depressed (down to the interior radial surface 1316), the plunger 1370 is rotated. This causes the lugs 1374 of the plunger to disengage from the lip 1358 of the push button member. In addition, it is contemplated that the push button member, once depressed, cannot be retracted from the barrel. This can be done, for example, using a stop surface near the outer end of the barrel (not shown).

When the plunger 1370 is no longer held in place by the push button member, the compression spring extends and pushes the plunger 1370 into the push button member 1350. It is contemplated that the compression spring is sized so that the plunger travels completely through the push button member, but will not push through the contact surface 1354 of the push button member. The liquid 1306 present in the reagent chamber falls into the reaction chamber and contacts the dry reagent 1308. The movement of the plunger into the push button member is intended to cause complete emptying of the contents of the reagent chamber into the reaction chamber. This mechanism can also provide forceful mixing of the wet reagent with the dry reagent, either induced by the spring action, initial chemical action, or both.

In some alternate embodiments, the spring also pushes at least some of the dry reagent into the reagent chamber (i.e. the interior volume of the push button member). For example, the dry reagent could be attached to the inner end 1373 of the plunger, and driven upwards by the spring.

Figure 20:
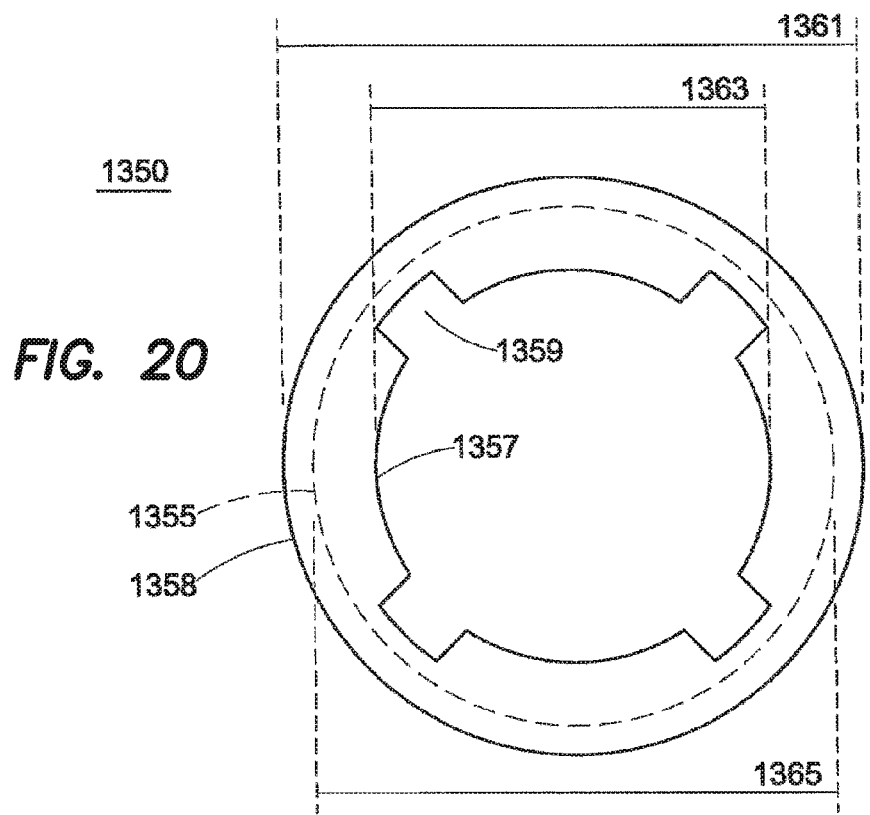
FIG. 20 is a bottom view showing the interior of the push button member in the syringe of FIG. 19.
Figure 21:
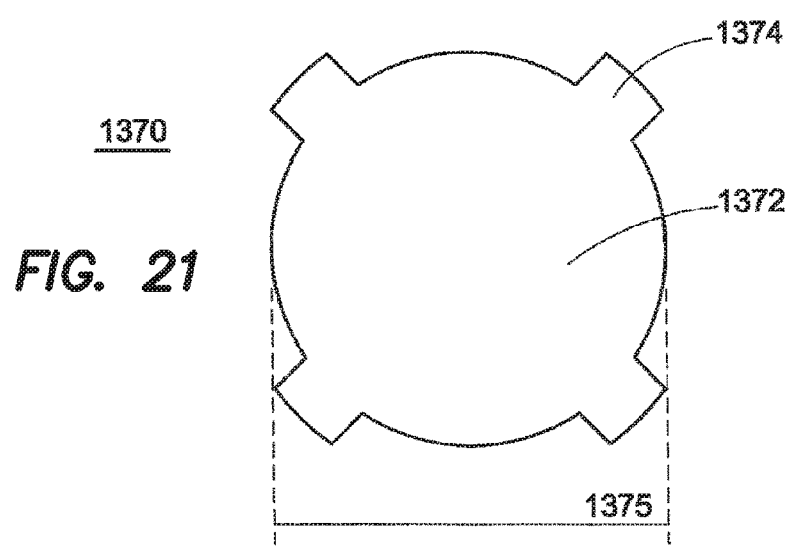
FIG. 21 is a top view of the stopper used in the syringe of FIG. 19.

FIG. 20 is a bottom view illustrating the interior of the push button member. As seen here, the interior surface 1357 of the sidewall forming the push button member includes four channels 1359 through which the lugs of the plunger can travel. FIG. 21 is a top view of the plunger 1370, showing the central body 1372 and the lugs 1374, which can travel in the channels of the push button member. Comparing these two figures, the outer circle of FIG. 20 is the lip 1358 of the push button member and has an outer diameter 1361. The inner diameter 1363 of the push button member is interrupted by the four channels. The dotted circle indicates the outer diameter 1365 of the sidewall exterior surface 1355. The central body of the plunger has a diameter 1375 which is less than the inner diameter 1363 of the push button member, with the lugs fitting into the channels. This permits the plunger to push the liquid in the push button member out and around the central body. It should be noted that the channels do not need to be straight, as illustrated here. For example, the channels may be angled to one side, i.e. twist in a helical manner. This might be desirable to add turbulence to the liquid reagent and improve mixing.

The combination of the solvent with bicarbonate and the citrate in the reaction chamber 1330 causes gas 1309 to be generated. It should be noted that due to the movement of the plunger, the reagent chamber could now be considered to be part of the reaction chamber. In addition, it should be noted that the dry reagent 1308 in FIG. 19 could be considered as restricting access to the orifice 1331. Upon dissolution, the orifice is clear and gas can enter the bottom end 1334 of the reaction chamber.

Once a threshold pressure is reached, the piston 1360 travels through the fluid chamber 1340, ejecting fluid from the syringe. The needle 1305 of the syringe is visible in this figure.

In some alternate contemplated embodiments, the diameter of the plunger including the lugs is less than the inner diameter 1363 of the push button member. In other words, channels are not needed on the inner sidewall of the push button member. In such embodiments, the barrel sidewall would provide a surface that holds the plunger in place until the push button is depressed to rotate the plunger. The shape and movement of the plunger would then cause turbulence in the liquid as the wet reagent flowed past the lugs into the reaction chamber. It is also contemplated that a stem could be attached to the plunger that extends into the reagent chamber, or put another way, the stem is attached to the outer end of the plunger. The stem may be shaped to cause turbulence and improve mixing.

It is also contemplated that the speed of the injection could be adjusted by the user. One way of doing this would be to control the speed at which the dry reagent and a wet reagent are mixed. This would adjust the speed of the gas-generating chemical reaction, and therefore the speed at which the force that pushes the piston is generated. This could be accomplished, for example, by adjusting the size of the opening between the reagent chamber and the reaction chamber. For example, an adjustable aperture could be placed beneath the plunger. The aperture would have a minimum size (to accommodate the spring), but could otherwise be adjusted. Another way of adjusting the speed of the injection would be to control the size of the reaction chamber. This would adjust the pressure generated by the chemical reaction (because pressure is force per area). For example, the sidewall of the reaction chamber could move inwards or outwards as desired to change the volume of the reaction chamber. Alternately, the interior radial surface 1336 could include an adjustable aperture to change the size of the orifice 1331 and the rate at which gas can enter the bottom end 1334 of the reaction chamber and push on the piston 1360. Both of these methods could be controlled by a dial on the syringe, which could mechanically adjust the speed of injection as desired by the user. It is possible that this would allow "on-the-fly" adjustment of the speed of injection.

It is also contemplated that a gas-permeable liquid-solid impermeable filter may be present that separates the piston from the lower chamber in the injection devices described herein. In this regard, the dry powder has been found in some situations to stick to the sides of the chamber. When the piston moves, remaining solvent falls below the level of the powder, such that further chemical reaction does not occur. It is believed that the filter should keep any dry solid reagent and liquid within the lower chamber to improve mixing.

Suitable materials for the injection devices of the present disclosure are known in the art, as are methods for making the injection devices.

The gas-generating chemical reaction used to generate force "on demand", as opposed to springs, which only store energy when compressed. Most autoinjectors hold a spring in a compressed position during "on the shelf" storage, causing parts to fatigue and to form over time. Another alternative to compressing the spring in manufacturing is to provide a cocking mechanism that compresses the spring prior to use. This adds another step to the process for using the spring-driven device. In addition, physically disabled users may have difficulty performing the cocking step. For example, many users of protein drugs are arthritic, or have other conditions that limit their physical abilities. The force needed to activate the gas-generating chemical reaction can be far less than that required to activate a spring-driven device or to cock the spring in a spring-driven device. In addition, springs have a linear energy profile. The force provided by the gas-generating chemical reaction can be non-linear and non-logarithmic. The speed of the chemical reaction can be controlled by (i) adjusting the particle size of the dry reagent; (ii) changing the particle shape of the dry reagent; (iii) adjusting the packing of the dry reagent; (iv) using mixing assist devices; and/or (v) altering the shape of the reaction chamber where the reagents are mixed.

It should be noted that silicone oil is often added to the barrel of the syringe to reduce the release force (due to static friction) required to move the piston within the barrel. Protein drugs and other drugs can be negatively impacted by contact with silicone oil. Siliconization has also been associated with protein aggregation. The forces generated by the chemical reaction obviate the need for application of silicone oil to the barrel of the syringe. In other words, no silicone oil is present within the barrel of the syringe.

When a solvent is used to form a medium for a chemical reaction between chemical reagents, any suitable solvent may be selected. Exemplary solvents include aqueous solvents such as water or saline; alcohols such as ethanol or isopropanol; ketones such as methyl ethyl ketone or acetone; carboxylic acids such as acetic acid; or mixtures of these solvents. A surfactant may be added to the solvent to reduce the surface tension. This may aid in improving mixing and the subsequent chemical reaction.

The following examples are for purposes of further illustrating the present disclosure. The examples are merely illustrative and are not intended to limit processes or devices made in accordance with the disclosure to the materials, conditions, or process parameters set forth therein.

EXAMPLE 1

A test rig was used for carrying out experiments. A standard prefilled syringe was filled with 1 ml fluid. A prefilled syringe was fitted with a 19 mm long and 27 gauge TW needle and stopped with a standard stopper. This syringe acted as the fluid chamber. Connected to the prefilled syringe was a reaction chamber syringe. A green piston rod and a push surface were used to apply force from the chemical reaction to the stopper. A one-way pressure valve was used to allow injection of solvent from a second "injector" syringe that acted as the reagent chamber. The set-up was clamped into the test fixture shown. A graduated pipette was used to measure the volume delivered versus time.

Two fluids were tested, water (1 cP) and silicone oil (73 cP). Water served as the low-viscosity fluid, silicone oil served as the high-viscosity fluid. One of these two fluids was added to the prefilled syringe depending on the experiment. To the reaction chamber syringe was added 400 mg $NaHCO_3$ and 300 mg citric acid, as dry powders. The injector syringe was filled with either 0.1 ml, 0.25 ml, or 0.5 ml water. The water was injected into the reaction syringe (the volume of the reaction syringe was adjusted based on the volume to be delivered by the injector syringe). The delivered volume versus time and total delivery time were measured. The pressure was calculated using the Hagen-Poiseuille equation and assumed there was 0.6 lb frictional force between the stopper and the prefilled syringe. Alternatively, the force on the prefilled syringe was determined by placing a load cell at the exit. The results are shown in Table 1 and were based on a minimum of at least three runs.

| Injector Syringe (ml water) | Time to Deliver 1 ml water (sec) | Time to Deliver 1 ml silicone oil (sec) |
|---|---|---|
| 0.1 | 5 | 24 ± 9.0 |
| 0.25 | 4.5 ± 0.5 | 16.38 ± 4.62 |
| 0.5 | 4 ± 1.0 | 9.5 ± 0.5 |
| 1.0 |  | 8.89 ± 0.19 |
| 2.0 |  | 6.5 ± 0.79 |
| 3.0 |  | 5.58 ± 0.12 |
| 4.0 |  | 6.54 ± 0.05 |

The chemical reaction syringe provided delivery of 1 ml water from the prefilled syringe in 5 seconds. The delivery time for the higher viscosity fluid depended on the volume of water injected from the injector syringe. Surprisingly, the delivery time was faster when the volume of water was greater. This was surprising because water, which does not participate in the reaction, served to dilute the reagents. Reaction kinetics, the production of $CO_2$, decrease as the concentration of reagents decreases. Thus, it was expected that a greater quantity of injected water would decrease the concentration and increase the delivery time due to slower production of $CO_2$. The results indicate the importance of the dissolution kinetics, which is the rate limiting step in this reaction. The dissolution was faster for higher volumes of water. Using 0.5 ml of water, high viscosity fluid can be delivered in 9 seconds.

Figure 22:
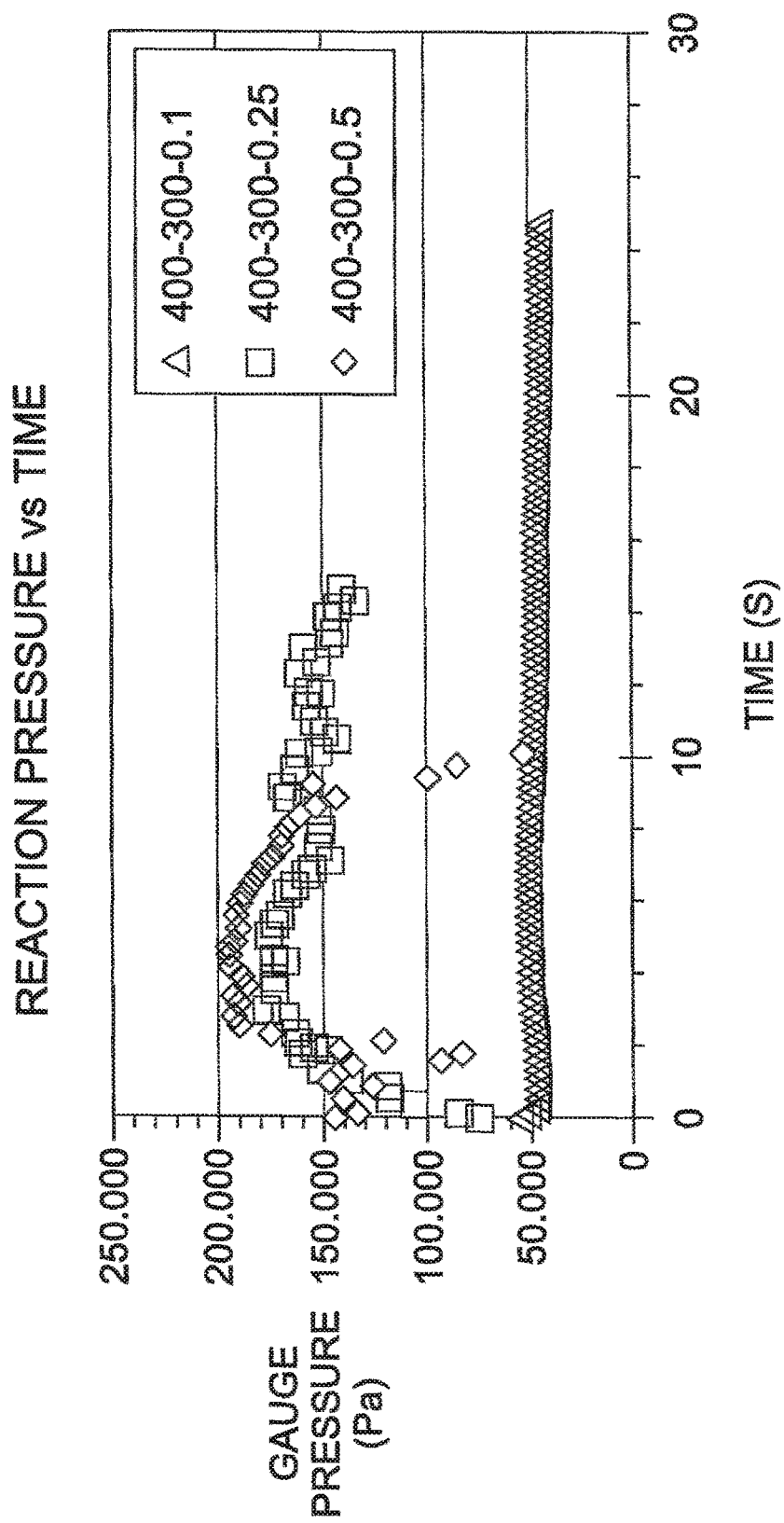
FIG. 22 is a graph showing the pressure versus time profile for delivery of silicone oil when different amounts of water are injected into a reaction chamber. The y-axis is Gauge Pressure (Pa), and the x-axis is Time (sec). The plot shows results for conditions where three different amounts of water were used—0.1 mL, 0.25 mL, and 0.5 mL.

FIG. 22 is a graph showing the pressure versus time profile for delivery of silicone oil when 0.1 ml (triangle), 0.25 ml (square), and 0.5 ml (diamond) of water was injected into the reaction chamber. This graph shows that a nearly constant pressure versus time profile could be obtained after a ramp-up period, although the impact of volume expansion dominated at longer times. These pressure versus time profiles were not exponential. A constant pressure versus time profile may allow for slower, even delivery of a high-viscosity drug, as opposed to a sudden exponential burst near the end of a delivery cycle.

EXAMPLE 2

Sodium chloride (NaCl) was used to enhance the release of gaseous $CO_2$ from the reaction solution in the reaction chamber, accelerating the increase in pressure. In control experiments, citric acid and $NaHCO_3$ were placed in the reaction syringe. A solution of 1.15 M $NaHCO_3$ in water was injected into the reaction syringe from the injector syringe. The empty volume in the reaction syringe was kept constant through all experiments. In experiments demonstrating the concept, NaCl was added to the reaction syringe. The chemical reaction was used to deliver 1 ml of water or silicone oil from the prefilled syringe. The delivered volume versus time and total delivery time were measured. The pressure was calculated using the Hagen-Poiseuille equation and assumed there was a 0.6 lb frictional force between the prefilled plunger and the syringe. Note that bicarbonate was present in the water injected into the reaction syringe, so that gas could be generated even if solid bicarbonate was not present in the reaction syringe itself. The results are shown in Table 2.

TABLE 2

| No | Reagents in Reaction Syringe (mg) | | | Injection Syringe (mL) | Time to Deliver 1 mL | Time to Deliver 1 mL |
|---|---|---|---|---|---|---|
| | Solid NaHCO$_3$ | Citric Acid | NaCl | 1.15M aq. NaHCO$_3$ | water (sec) | silicone oil (sec) |
| 1 | 350 | 304 | 0 | 0.5 | 1.38 ± 0.05 | 8.3 ± 0.8 |
| 2 | 350 | 304 | 121 | 0.5 | 1.69 ± 0.03 | 7 ± 1 |
| 3 | 50 | 76 | 0 | 0.5 | 4 | 13 |
| 4 | 50 | 76 | 121 | 0.5 | 4.9 ± 0.6 | 11 |
| 5 | 0 | 38 | 0 | 0.5 | 24 ± 1 | 41 ± 7 |
| 6 | 0 | 38 | 121 | 0.5 | 9 ± 2 | 20.5 ± 0.5 |

Salt served to significantly enhance the delivery rate, particularly for systems that used smaller amounts of reagent. A high viscosity fluid could be delivered in 6 to 8 seconds using the chemical reaction. This is significantly faster than what can be achieved with standard auto-injectors that employ mechanical springs.

Figure 23:
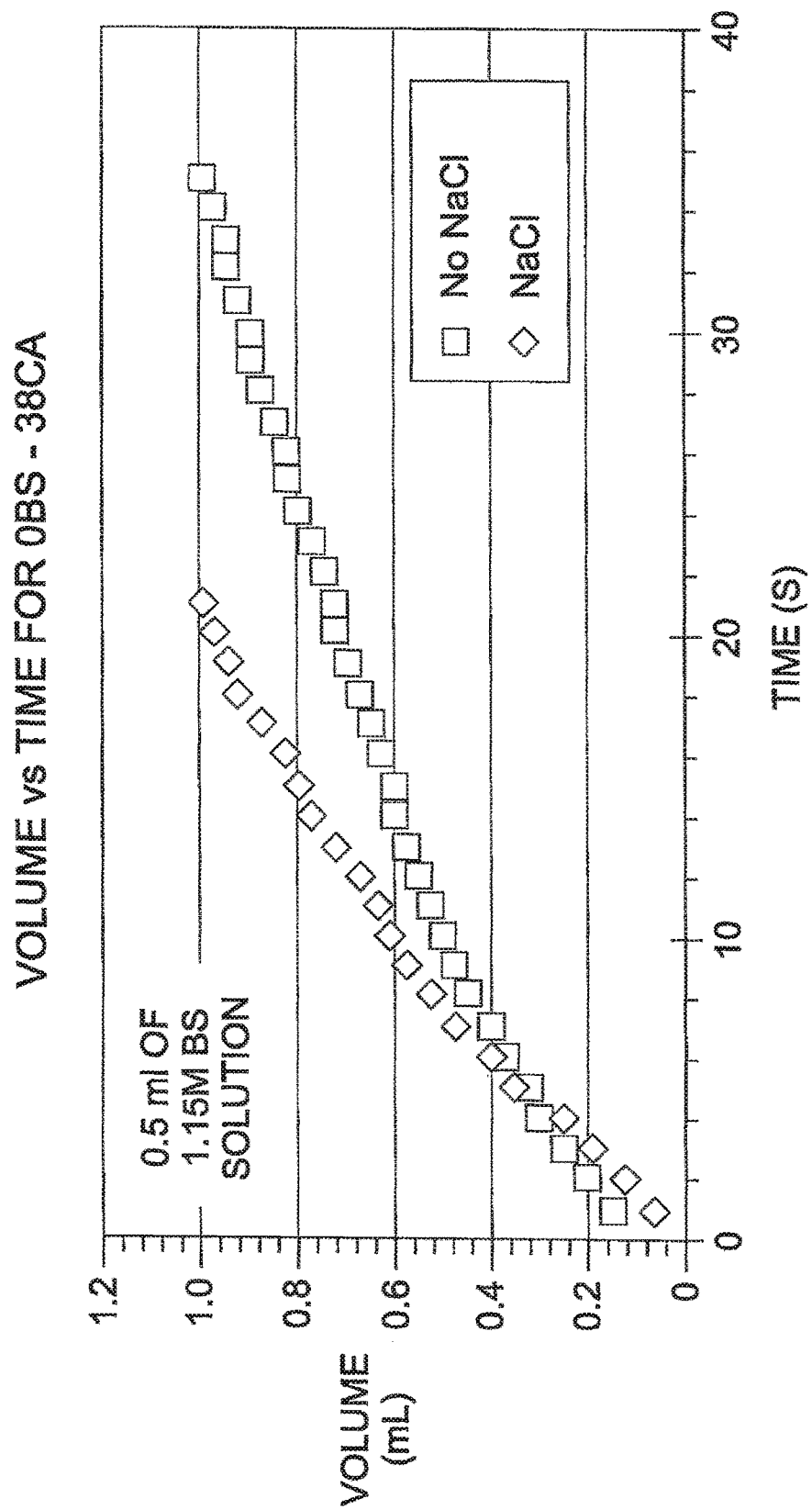
FIG. 23 is a graph showing the volume versus time profile for delivery of 73 cP silicone oil when a release agent (NaCl) is added to the reaction chamber. The y-axis is Volume (ml), and the x-axis is Time (sec).

FIG. 23 shows the delivered volume versus time profile for experiment Nos. 5 and 6 of Table 2. A high viscosity fluid was delivered in 20 seconds using a system having a footprint of less than 1 cm3. The delivery rate (i.e. slope) was also relatively constant. The small footprint enables a variety of useful devices.

EXAMPLE 3

Several different reagents were screened to determine, how the pressure versus time profile could be modified. Generally, reagents with two different dissolution rates were created by combining NaHCO$_3$ with two different surface areas. High surface area NaHCO$_3$ was produced by freeze drying a 1.15 M solution; this material had a faster dissolution rate than as-received NaHCO$_3$ powder.

Reagents

The following reagents were used: as-received baking soda (NaHCO$_3$), citric acid, freeze-dried baking soda, Alka-Seltzer, or as-received potassium bicarbonate (KHCO$_3$). The as-received baking soda was also tested as a powder, or in a tablet form. The tablet form had a decreased surface area.

The freeze-dried baking soda was formulated by preparing 125 ml of saturated baking soda aqueous solution (1.1 SM). The solution was poured into a 250 ml crystallization dish and covered with a Kimwipe. The solution was placed in a freeze dryer and was ramped down to −40° C. and held for two hours. The temperature remained at −40° C., and a vacuum was applied at 150 millitorrs (mTorr) for 48 hours. [0181] Alka-Seltzer tablets (Effervescent Antacid & Pain Relief by Kroger) were broken up using a mortar and pestle into a coarse powder.

Baking soda tablets were prepared by pouring 400 mg of as-received baking soda powder in a die to produce a tablet with a 1 cm diameter. The die was swirled around to move the powder to give an even depth across the 1 cm. The die was placed in a press and held at 13 tons pressure for 1 minute. Tablets weighing 40 mg and 100 mg were broken from the 400 mg tablet.

The Apparatus and Plan

The previously described test rig was used. The 3 ml injection syringe was filled with 0.5 ml of de-ionized water. The 10 ml reaction syringe was connected to the injection syringe by luer locks and a valve, and then clamped down tightly in the apparatus. A load cell was attached to the plunger rod so the reaction syringe plunger presses on it during the test. This recorded the applied force from the reaction while displacing the fluid in the prefilled syringe.

The fluid from the prefilled syringe was displaced into a graduated syringe which was video recorded. This observed the change in volume of the fluid over time. The fluids were water (1 cP) or silicone oil (73 cP), which were displaced through a 27 gauge thin-walled prefilled syringe and had a volume of 1 milliliter (ml).

Two measurements were acquired while during each test: the force on the prefilled syringe using a load cell and the change in volume of the prefilled syringe by measuring the dispensed volume with time. The average volume vs. time curve was plotted to show how each reaction changed the volume in the prefilled syringe. The pressure vs. time curve using the Hagen-Poiseuille equation was provided by calculating the flow rate from the volume vs. time curve. To account for the friction in the prefilled syringe, 94,219 Pa was added (which is equivalent to 0.6 lb). This calculated pressure inside the prefilled syringe (3 mm radius) so the hydraulic equation was used ($P_1A_1=P_2A_2$) to calculate the pressure inside the reaction syringe (6.75 mm diameter). This was used to check the measurement made by the load cell.

Another pressure vs. time curve was produced by using the force in the load cell measurement and dividing by the area of the reaction plunger. This has been shown to provide much cleaner and reproducible data than the calculation by Hagen-Poiseuille.

To see how the pressure changed with volume, pressure vs. volume curves were produced. The pressures used were those calculated by the load cell measurements. The reaction volume was calculated using the change of volume in the prefilled syringe. The volume of the reaction syringe (VR) could be determined from the dispensed volume in the prefilled syringe (Vp) at time t.

Finally, the reaction rate while dispensing the fluid was found by using the ideal gas law where PR is the pressure calculated from the load cell, VR is the volume of the reaction syringe, R is the universal gas constant (8.314 $Jmol^{-1}K^{-1}$), and T is the temperature, 298K.

The Tests

The baseline formulation was 400 mg of baking soda, 304 mg of citric acid, and 0.5 ml of de-ionized water as described in Example 1. This formulation produces 4.76×10-3 moles of $CO_2$ assuming 100% yield. The ingredients of all tests were formulated to produce the same 4.76×10-3 moles of $CO_2$ assuming 100% yield. Four sets of tests were performed.

The first set used as-received baking soda (BSAR) and freeze-dried baking soda (BSFD). Their relative amounts were varied in increments of 25%. 304 mg citric acid was also included in each formulation. Table 3A provides the target masses of the baking soda for these tests.

TABLE 3A

| | Target Mass [mg] | |
|---|---|---|
| Test | BSAR | BSFD |
| 100% BSAR | 400 | 0 |
| 75% BSAR | 300 | 100 |
| 50% BSAR | 200 | 200 |
| 25% BSAR | 100 | 300 |
| 100% BSFD | 0 | 400 |

The second set used as-received baking soda and Alka-Seltzer. The amount of as-received baking soda was varied in increments of 25%. The stoichiometric amount of citric acid was added. Alka-Seltzer is only approximately 90% baking soda/citric acid. Therefore, the total mass of Alka-Seltzer added was adjusted to obtain the required mass of baking soda/citric acid. Table 3B provides the target masses of each ingredient for these tests.

TABLE 3B

| Test | Target Weight [mg] | | |
|---|---|---|---|
| | Baking Soda | Citric Acid | Alka-Seltzer |
| 100% BSCA | 400 | 304 | 0 |
| 75% BSCA | 300 | 228 | 196 |
| 50% BSCA | 200 | 152 | 392 |
| 25% BSCA | 100 | 76 | 586 |
| 100% Alka-Seltzer | 0 | 0 | 777 |

The third set used as-received baking soda and as-received potassium bicarbonate. The mass of citric acid was maintained at 304 mg throughout the tests. Due to the heavy molar mass of potassium bicarbonate (100.1 g/mol as opposed to baking soda's 84.0 g/mol), more mass is required to generate the same moles of $CO_2$. Table 3C provides the target masses (in mg) of each ingredient for these tests.

TABLE 3C

| Test | Baking Soda | Potassium Bicarbonate |
|---|---|---|
| 100% BS | 400 | 0 |
| 50% BS | 200 | 239 |
| 100% KHCO3 | 0 | 477 |

The fourth set used the baking soda tablets. The stoichiometric amount of citric acid was used. No other reagents were added. Table 3D provides the target masses (in mg) of each ingredient for these tests.

TABLE 3D

| Test | Baking Soda Tablet | Citric Acid |
|---|---|---|
| 400BS-304CA | 400 | 304 |
| 100BS-76CA | 100 | 76 |
| 40BS-30CA | 40 | 30 |

Results of the Tests

First Set: as-received baking soda (BSAR) and freeze-dried baking soda (BSFD).

The freeze-dried baking soda powder appeared coarse relative to the as-received baking soda powder. It was also less dense: 400 mg of the freeze-dried powder occupied 2 ml in the reaction syringe, whereas the as-received powder only occupied 0.5 ml. Due to the volume of material, the smaller volume of water (0.5 ml) could not come into contact with all of the freeze-dried baking soda. There was solid freeze-dried baking soda after each experiment. Only silicone oil in the prefilled syringe was tested.

In addition to the four test formulations described above, a fifth formulation was run where the freeze-dried sample was inserted first. It was followed by the citric acid and then the as-received powder. It was labeled as "50% BSAR Second". This formulation permitted the injected water to come into contact first with the freeze-dried powder, then contact and dissolve the citric acid and the as-received powder. The time needed to displace 1 ml of the silicone oil is listed in Table 3E.

TABLE 3E

| Formulation | Time (sec) |
|---|---|
| 100% BSAR | 10 |
| 75% BSAR | 13 |
| 50% BSAR | 11 |
| 50% BSAR Second | 22 |
| 100% BSFD | 14 |

Figure 24:
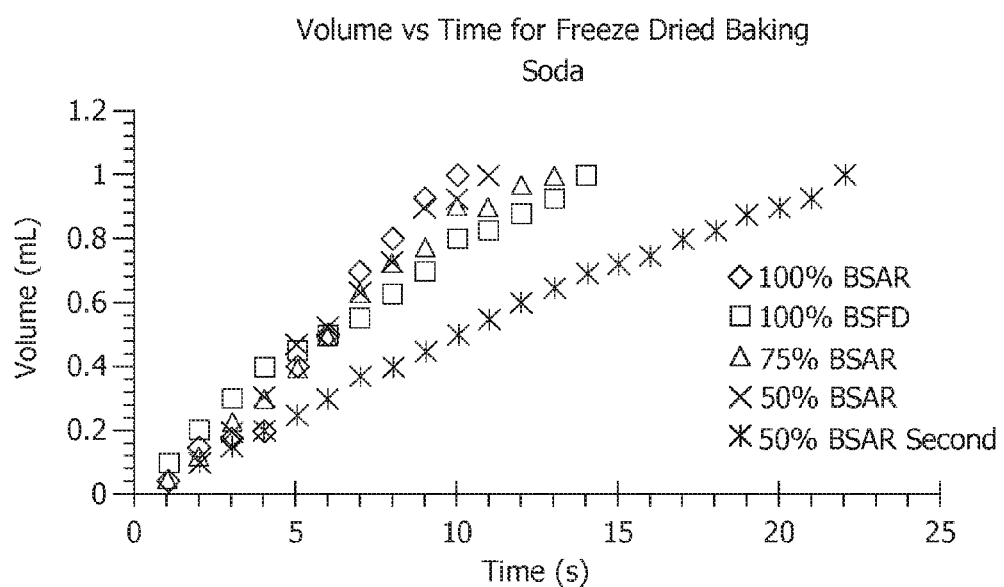
FIG. 24 is a volume vs. time graph for delivery of a 73 cP silicone fluid in which the use of modifying or mixing bicarbonate morphology is shown: reaction chamber contains 100% as received, 100% freeze-dried, 75% as-received/25% freeze dried, or 50% as-received/50% freeze dried.

The volume vs. time graph is seen in FIG. 24. It appeared that the 100% freeze-dried powder was initially faster than the 100% as-received powder but slowed over time. The as-received powder took 10 seconds to displace 1 ml, and the freeze-dried powder took 14 seconds. As expected, the trials with mixed amounts were found to have times between the two extremes.

Figure 25:
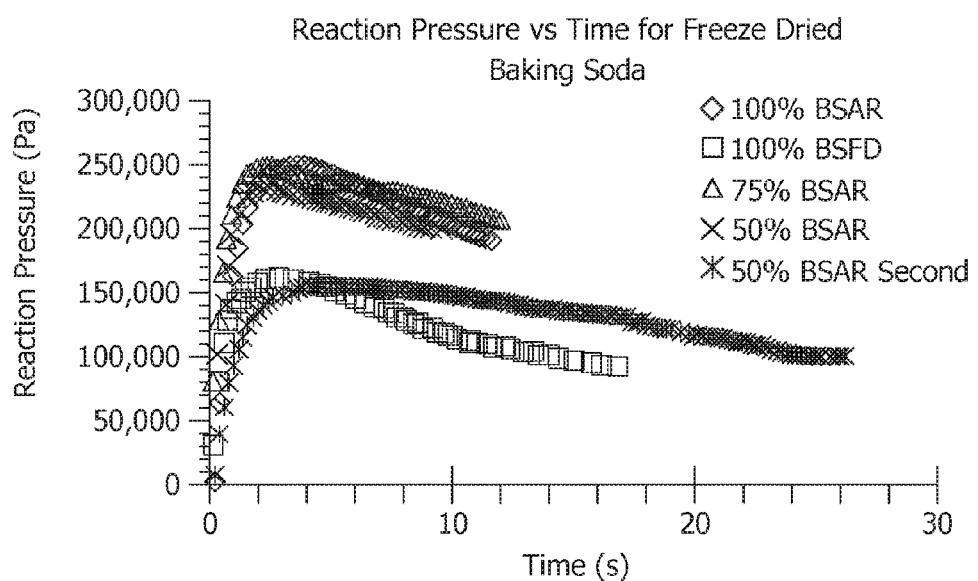
FIG. 25 is a pressure vs. time graph for delivery of a 73 cP silicone fluid in which the use of modifying or mixing bicarbonate morphology is shown: reaction chamber contains 100% as received, 100% freeze-dried, 75% as-received/25% freeze dried, or 50% as-received/50% freeze dried.

The pressure vs. time graph is given in FIG. 25. The formulations with 100% BSAR showed a maximum pressures nearly 100,000 Pa higher than those with 100% BSFD. In comparison, using "75% BSAR" gave a faster pressure increase and slower decay. For ease of comparison, the pressures were normalized and plotted in FIG. 26 and FIG. 27 (two different time periods).

Figure 26:
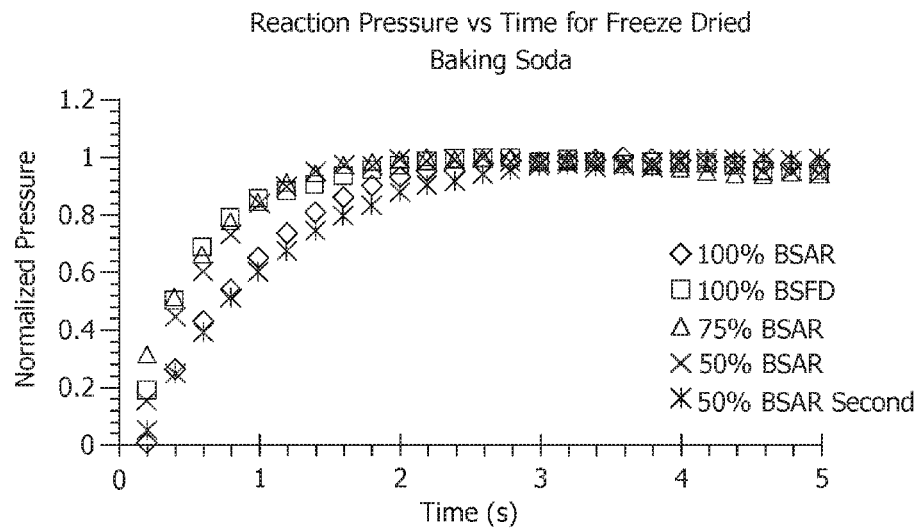
FIG. 26 is a normalized pressure vs. time graph delivery of a 73 cP silicone fluid during an initial time period. The use of modifying or mixing bicarbonate morphology is shown: reaction chamber contains 100% as received, 100% freeze-dried, 75% as-received/25% freeze dried, or 50% as-received/50% freeze dried.

The 100% BSAR had an initial slow reaction rate compared to the 75% BSAR and 50% BSAR formulations. This suggests the freeze-dried baking soda (BSFD) dissolves and reacts faster, and this is seen in FIG. 26. However, FIG. 25 shows that as the freeze-dried baking soda content increases, a lower maximum reaction pressure is obtained. It was observed that 200 mg of the freeze-dried baking soda occupies 1 ml of space, so the 0.5 ml of de-ionized water cannot contact all of the freeze-dried powder before the generated gas moves the plunger, leaving the dry powder behind stuck on the side of the chamber. Put another way, not all of the freeze-dried baking soda can be reacted, resulting in less $CO_2$ production. It was estimated for the 100% BSFD trial that only a quarter of the reagent dissolved.

In the 50% BSAR Second trial, when the freeze-dried baking soda was added first followed by the citric acid and as-received baking soda, much of the powder remained solid, resulting in a lower pressure. The low initial reaction was most likely caused by the 0.5 ml of water diffusing through the 1 ml of freeze-dried baking soda powder before reaching and dissolving the citric acid. Surprisingly, this test was the closest of the trials in this set to providing a constant pressure profile.

The maximum pressure obtained was at approximately 0.8 ml $CO_2$ volume for the 50% BSAR and 75% BSAR formulations. These formulations also had the fastest rate in the pressure vs. time graphs (see FIG. 26). The remaining formulations had maximum pressures at approximately 1.2 ml $CO_2$.

Figure 27:
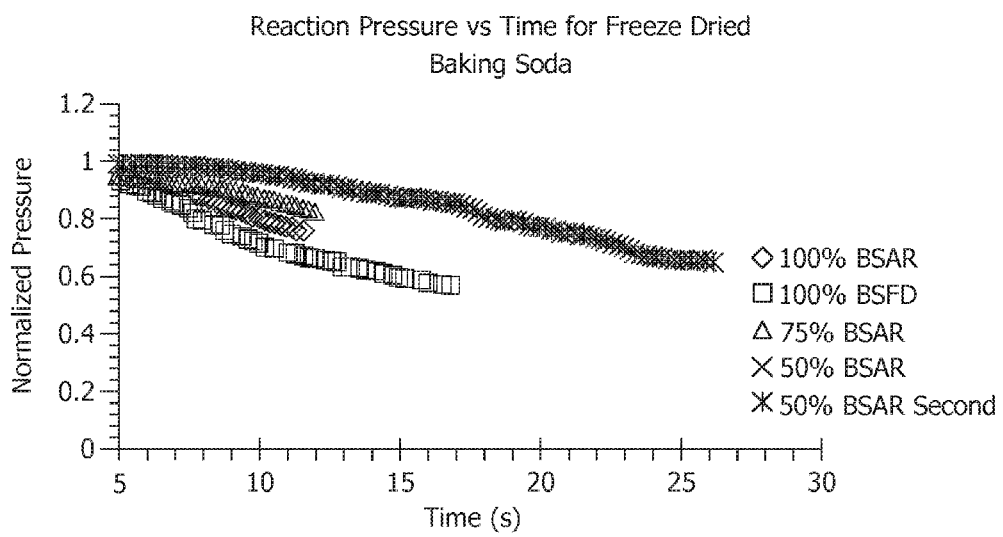
FIG. 27 is a normalized pressure vs. time graph delivery of a 73 cP silicone fluid during a second time period. The reaction chamber contained bicarbonates with different morphology or mixed morphology: 100% as received, 100% freeze-dried, 75% as-received/25% freeze dried, and 50% as-received/50% freeze dried.

Interestingly, when looking at FIG. 27, the "50% BSAR Second" showed a distinct pressure vs. time profile (Pa/s in FIG. 27), but had approximately the same pressure vs. volume profile as the 100% BSFD. Referring back to Table 3E, it took approximately 8 seconds longer for the "50% BSAR Second" to displace the 1 ml of silicone oil, so its pressure curve is "drawn out" relative to the 100% BSFD, and it had a different flow rate. It is unclear why this occurred if the pressure vs. volume curves are the same. Other experiments for this trial failed due to leaking or clogging, and it is possible the pressure profile was caused by increased friction in the prefilled syringe.

Table 3F shows the reaction rates fitted to $y=ax^2+bx$.

TABLE 3F

| Formulation | First Term (a) | Second Term (b) |
|---|---|---|
| 100% BSAR | 0 | $5 \times 10^{-5}$ |
| 75% BSAR | 0 | $4 \times 10^{-5}$ |
| 50% BSAR | 0 | $4 \times 10^{-5}$ |
| 50% BSAR Second | $-5 \times 10^{-7}$ | $2 \times 10^{-5}$ |
| 100% BSFD | $-1 \times 10^{-6}$ | $2 \times 10^{-5}$ |

The 100% BSAR, 75% BSAR, and 50% BSAR curves have approximately the same linear reaction rate. The "50% BSAR Second" forms a second order polynomial. The "100% BSFD" appears to be parametric; it has the same linear rate as 100% BSAR and the other two, and then the slope suddenly decreases after 5 seconds and converges with "50% BSAR Second."

It is believed that the second order reaction rates are caused by loss of material and not the rate of reaction itself. In the "100% BSFD" trial, the freeze-dried baking soda had a volume of 2 ml. When the 0.5 ml of water was injected, there was plenty of material to dissolve and react. After 5 seconds, the total reaction volume had opened to 3.27 ml. The syringe had opened up far enough that the water was no longer in contact with the solid freeze-dried baking soda (stuck to the side of the chamber). All that could react was what had been dissolved, and this slowed the rate of reaction. The same was true for the "50% BSAR Second", except it had to diffuse through 1 ml of the freeze-dried baking soda before dissolving the citric acid, resulting in a slower reaction altogether.

Second Set: as-received baking soda and Alka-Seltzer.

Figure 28:
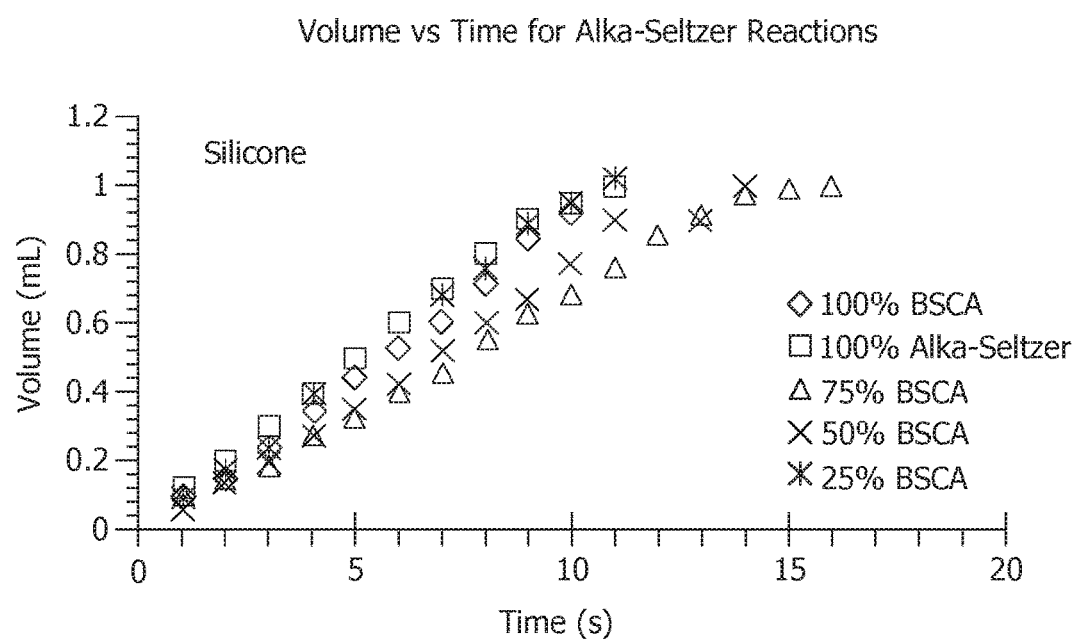
FIG. 28 is a volume vs. time graph for delivery of a 73 cP silicone fluid in which the use of reagents with different dissolution rate or structure is shown. The engine contained either 100% as-received baking soda and citric acid powder, 100% alka seltzer adjusted for similar stoichiometric ratio, 75% as-received powders/25% Alka Seltzer, 50%, 25% as-received powders/75% alka seltzer.
Figure 29:
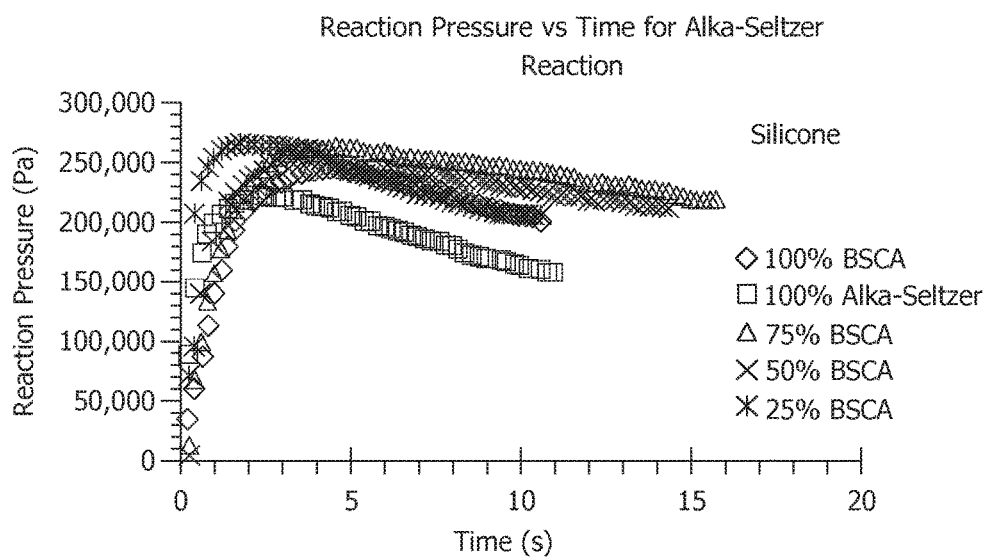
FIG. 29 is a pressure vs. time graph for delivery of a 73 cP silicone fluid in which the use of reagents with different dissolution rate or structure is shown. The engine contained either 100% as-received baking soda and citric acid powder, 100% alka seltzer adjusted for similar stoichiometric ratio, 75% as-received powders/25% Alka Seltzer, 50%, 25% as-received powders/75% alka seltzer.

The volume vs. time graph is seen in FIG. 28 for silicone oil, and in FIG. 29 for water as the injected fluids respectively. The time needed to displace 1 ml of each fluid is listed in Table 3G, the error in time measurement is estimated to be half a second.

TABLE 3G

| | Time (sec) | |
|---|---|---|
| Formulation | Silicone | Water |
| 100% BSCA | 11 ± 0.95 | 3 |
| 75% BSCA | 14.78 ± 1.35 | 3.2 |
| 50% BSCA | 12.5 ± 2.12 | 2.27 ± 0.47 |
| 25% BSCA | 10.11 ± 1.02 | 3 |
| 100% Alka-Seltzer | 11 | 2 |

The times for displacement of water are difficult to compare because they are all within one second of each other. The volume profiles for 100% BSCA, 25% BSCA, and 100% Atka-Seltzer had the fastest times to displace 1 ml of silicone oil. The 100% BSCA appeared to start slowly and then speed up. The 50% BSCA and 75% BSCA were found to have the slowest times. They appeared to slow down as the displacement proceeded.

Figure 30:
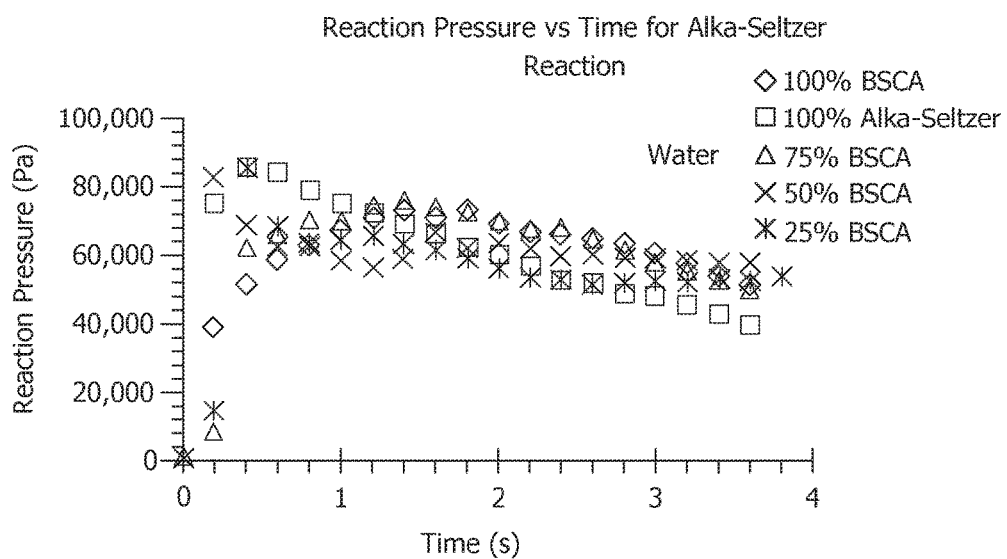
FIG. 30 is a pressure vs. time graph for the delivery of a 1 cP water fluid in which the use of reagents with different dissolution rate or structure is shown. The engine contained either 100% as-received baking soda and citric acid powder, 100% alka seltzer adjusted for similar stoichiometric ratio, 75% as-received powders/25% Alka Seltzer, 50%, 25% as-received powders/75% alka seltzer.
Figure 31:
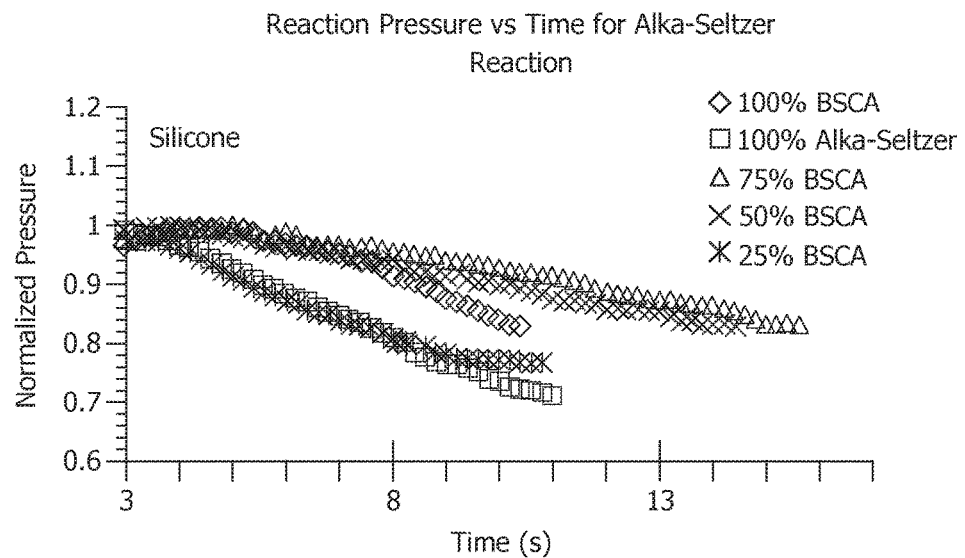
FIG. 31 is a normalized pressure vs. time graph for delivery of a 73 cP silicone fluid in which the use of reagents with different dissolution rate or structure is shown. The engine contained either 100% as-received baking soda and citric acid powder, 100% alka seltzer adjusted for similar stoichiometric ratio, 75% as-received powders/25% Alka Seltzer, 50%, 25% as-received powders/75% alka seltzer. The pressure is normalized by normalizing the curves in FIG. 29 to their maximum pressure.

The pressure vs. time graph is given in FIG. 30 for silicone oil, and in FIG. 31 for water as the injected fluids respectively. The 100% BSCA had the slowest initial pressure rise. This was expected, since Alka-Seltzer is formulated to allow fast diffusion of water into the tablet. The 75% BSCA and 50% BSCA had the second and third greatest maximum pressure, respectively, for silicone oil. However, these two formulations took the longest to displace 1 ml of silicone oil. Their pressures also had the slowest decay. This is most likely due to increased friction in the syringe.

The curves in FIG. 31 for water are within a reasonable error of each other. However, they were greater than the estimated pressures by Hagen-Poiseuille, which calculated the maximum pressure to be 51,000 Pa by the 100% Alka-Seltzer formulation. High friction was not observed during testing. It is not known why there was a difference in the pressure measured by the load cell and the theoretical pressure calculated by Hagen-Poiseuille.

Figure 32:
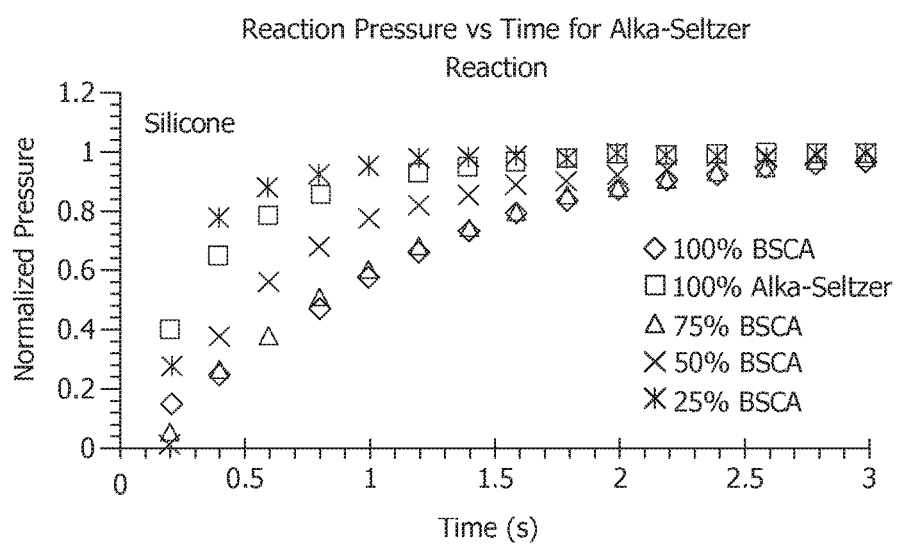
FIG. 32 is a normalized pressure vs. time graph expanding the first 3 seconds of FIG. 31.
Figure 33:
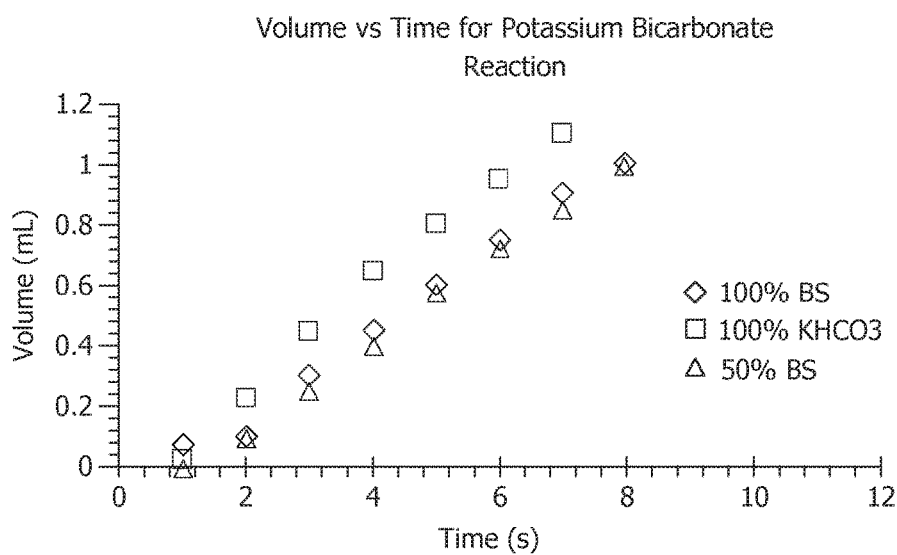
FIG. 33 is a volume vs. time graph for delivery of a 73 cP silicone fluid in which the reaction chamber contained either sodium bicarbonate (BS), potassium bicarbonate, or a 50/50 mixture.

Normalized pressure vs. time graphs are provided for silicone oil in FIG. 32, with the first 3 seconds expanded in FIG. 33. The pressure decay rate for silicone oil is provided in Table 3H.

TABLE 3H

| Formulation | Decay Rate (Pa/s) |
|---|---|
| 100% BSCA | 6,854 |
| 75% BSCA | 4,373 |
| 50% BSCA | 3,963 |
| 25% BSCA | 9,380 |
| 100% Alka-Seltzer | 10,695 |

For silicone oil, the 100% BSCA and the 75% BSCA had the same normalized pressure increase, but different decays. As explained above, the 75% BSCA may have undergone more friction causing the change in volume to slow and hold pressure longer. The same was true for the 50% BSCA, which had the same decay as 75% BSCA. Surprisingly, the pressure increase for 50% BSCA fit just between 100% BSCA and 100% Alka-Seltzer. This may indicate that friction does not affect the pressure increase. The 100% Alka-Seltzer and 25% BSCA had the same pressure profiles with the fastest pressure increase and fastest decay. The 100% BSCA also appeared to have the same decay as these two formulations.

For water, it was found that higher ratios of Alka-Seltzer to BSCA resulted in relatively less pressure decay. The 100% Alka Seltzer had a fast pressure increase but quickly decayed along with 100% BSCA" and 75% BSCA. However, 25% BSCA and 50% BSCA had fast pressure increase and less pressure decay than the other formulations.

For silicone oil, the 100% Alka-Seltzer, 50% BSCA, and 75% BSCA all peaked at approximately 1.2 ml of $CO_2$ volume. The 25% BSCA peaked at approximately 0.8 ml. The 100% BSCA did not reach maximum pressure until approximately 1.6 ml. This was slightly different than the "100% BSAR" in the first set of tests, which used the exact same formulation but reached its maximum pressure at a $CO_2$ volume of 1.2 ml.

Table 3I shows the reaction rates for CO2 production during injection of silicone oil fitted to $y=ax^2+bx$.

TABLE 3I

| Formulations | First Term (a) | Second Term (b) |
|---|---|---|
| 100% BSCA | 0 | $4 \times 10^{-5}$ |
| 75% BSCA | 0 | $3 \times 10^{-5}$ |
| 50% BSCA | 0 | $3 \times 10^{-5}$ |
| 25% BSCA | 0 | $4 \times 10^{-5}$ |
| 100% Alka-Seltzer | $-2 \times 10^{-6}$ | $6 \times 10^{-5}$ |

All formulations except 100% Alka-Seltzer formed linear reaction rates for silicone oil. The high friction in the prefilled syringe used to test 75% BSCA and 50% BSCA caused a high pressure, which may have reduced the reaction rate to $3\times10^{-5}$ mol/s. The 100% BSCA and 25% BSCA had the same reaction rate at $4\times10^{-5}$ mol/sec. 100% Alka-Seltzer resulted in a second order polynomial. It initially had the same reaction rate as the other formulations, but the slope decreased in the last few seconds. When the reaction was finished, the solution was much thicker than the other formulations.

The 100% BSCA was slightly slower than the previous experiment with freeze-dried baking soda, 100% BSAR (see Table 3F), by $1\times10^{-5}$ mol/sec. This may have caused the slower time to displace the silicone and possibly the maximum pressure at a greater $CO_2$ volume at 1.6 ml.

Third Set: as-received baking soda and as-received potassium bicarbonate.

Figure 34:
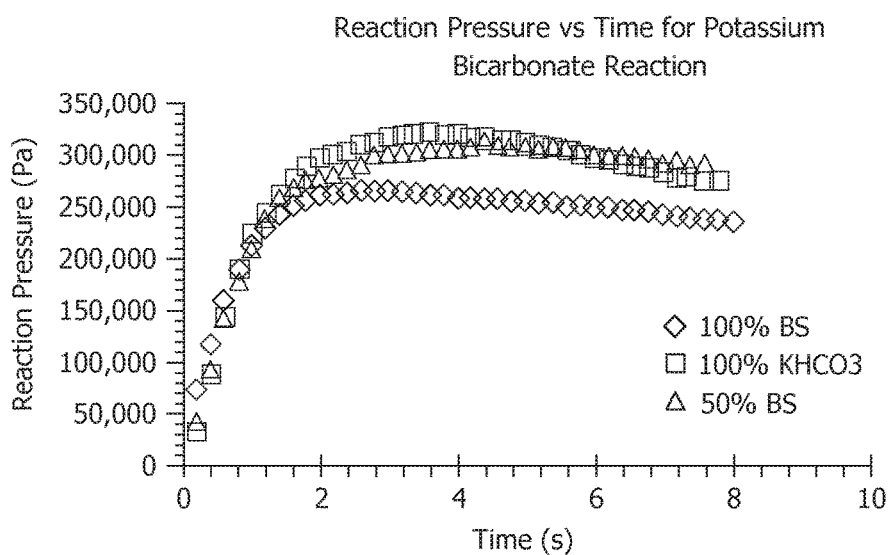
FIG. 34 is a pressure vs. time graph for the third set of tests; delivery of a 73 cP silicone fluid in which the reaction chamber contained either sodium bicarbonate (BS), potassium bicarbonate, or a 50/50 mixture.

The volume vs. time graph is seen in FIG. 34, for silicone oil. The time needed to displace 1 ml of each fluid is listed in Table 3J.

TABLE 3J

| Formulation | Time (sec) |
| --- | --- |
| 100% BS | 8.00 |
| 50% BS | 8.00 |
| 100% KHC03 | 6.33 |

The 100% $KHCO_3$ was the fastest to displace the 1 ml of silicone at 6.33 seconds. The 100% BS and 50% BS displaced the same volume at a time of 8.00 seconds.

Figure 35:
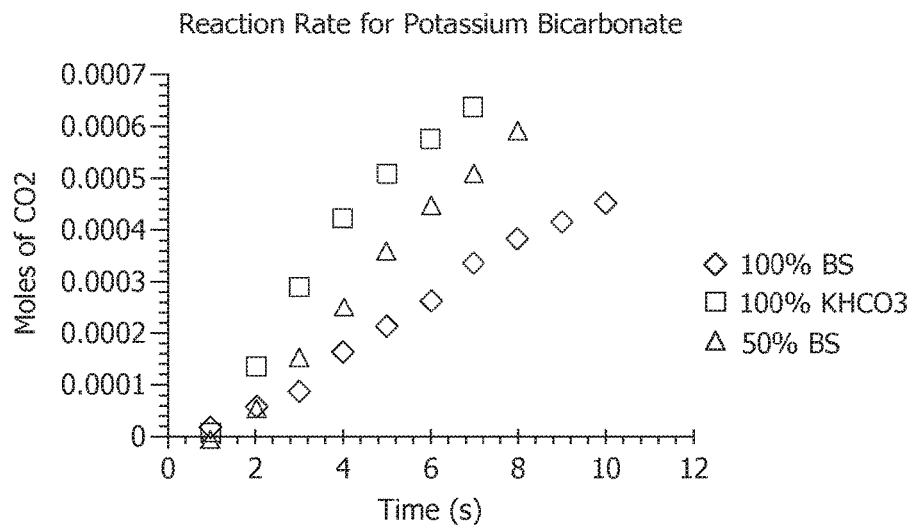
FIG. 35 is a reaction rate graph for the third set of tests; delivery of a 73 cP silicone fluid in which the reaction chamber contained either sodium bicarbonate (BS), potassium bicarbonate, or a 50/50 mixture.

The pressure vs. time graph is given in FIG. 35. The pressure decay rate for silicone oil is provided in Table 3K.

TABLE 3K

| Formulation | Pressure Decay (Pa/sec) |
| --- | --- |
| 100% BS | 6,017 |
| 50% BS | 7,657 |
| 100% KHC03 | 11,004 |

The 100% BS formulation only reached a maximum pressure of approximately 250,000 Pa, while the other two formulations had a maximum pressure of approximately 300.000 Pa. The 100% $KHCO_3$ and 50% BS formulations (each containing potassium bicarbonate) continued increasing in pressure for a few seconds after the 100% BS reached its maximum. The 50% BS formulation initially had less pressure as expected but was able to maintain a higher pressure after 6 seconds compared to the 100% $KHCO_3$. The results showed that using a mixture of sodium and potassium bicarbonate can produce higher pressures and slow decays.

The 100% BS had a peak pressure somewhere between 0.6 and 1.8 ml of $CO_2$. The curves for 50% BS and 100% $KHCO_3$ were very different from the other pressure vs. volume graphs previously seen herein. Instead of peaking at approximately 1.2 ml of $CO_2$ volume and decaying, they tended to continue increasing in pressure at greater $CO_2$ volumes. The 50% BS and 100% KHC03 formulations peaked at approximately 2.0 and 3.2 ml of $CO_2$ volume, respectively.

Figure 36:
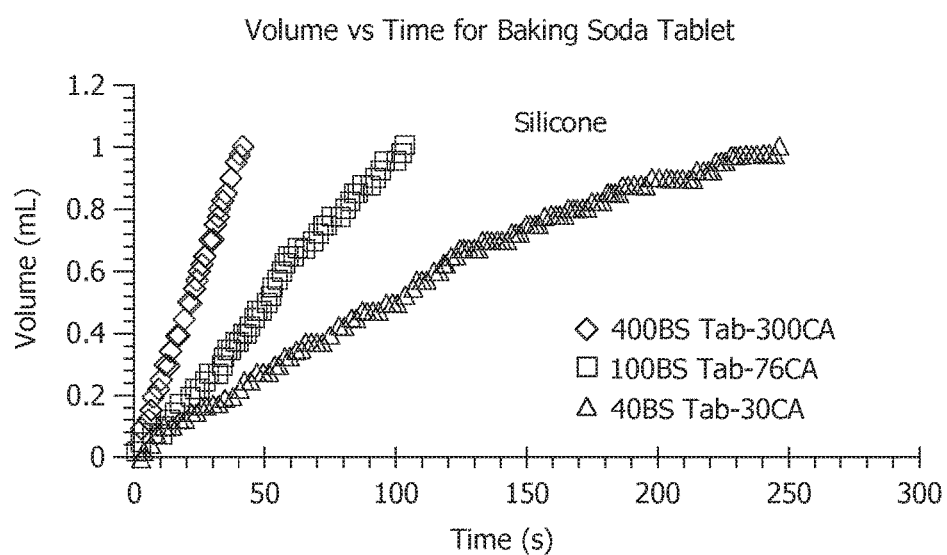
FIG. 36 is a volume vs. time graph for a fourth set of tests for silicone oil.

A reaction rate graph is given in FIG. 36 for silicone oil, showing the total number of moles $CO_2$ produced over time. Table 3L shows the reaction rates fitted to y=bx.

TABLE 3L

| Formulation | Rate (mol/sec) |
| --- | --- |
| 100% BS | 5 × 10–0 |
| 50% BS | 9 × 10–0 |
| 100% KHC03 | 1 × 10–4 |

They appeared to be linear reaction rates with 100% BS at $5\times10^{-5}$ mol/sec (the same rate from the experiments above). Using 100% potassium bicarbonate had twice the rate as baking soda, although it appeared that the reaction rate started to decrease at approximately 4 seconds.

Fourth Set: baking soda tablets.

The volume vs. time graph is seen in FIG. 37 for silicone oil. The time needed to displace 1 ml of each silicone oil or water is listed in Table 3M.

TABLE 3M

| Baking Soda Tablet (mg) | Time (sec) | |
| --- | --- | --- |
| | Silicone | Water |
| 400 | 42 | 25.67 |
| 100 | 104 | 78 |
| 40 | 247 | 296 |

For both silicone oil and water, using 400 mg and 100 mg baking soda tablets and the stoichiometric citric acid resulted in nearly straight lines. Packing the baking soda into dense tablets significantly decreased reaction rates, and thus increased injection times, relative to other baking soda experiments. Table 3N shows the reaction rates fitted to $y=ax^2+bx$.

TABLE 3N

| | Silicone Oil | | Water | |
| --- | --- | --- | --- | --- |
| Formulations | First Term (a) | Second Term (b) | First Term (a) | Second Term (b) |
| 400BS | 0 | $4 \times 10^{-6}$ | $3 \times 10^{-8}$ | $2 \times 10^{-7}$ |
| 100BS | 0 | $7 \times 10^{-7}$ | N/A | N/A |
| 40BS | $-4 \times 10^{-10}$ | $2 \times 10^{-7}$ | N/A | N/A |

For silicone oil, the 400 mg BS tablet showed the linear reaction rate as $4\times10^{-6}$ mol/sec. The 100 mg baking soda tablet was linear for almost 87 seconds until it suddenly stopped producing gaseous $CO_2$. The reaction rate for the 40 mg tablet was a second order polynomial and very slow. It reached a total of $2\times10^{-5}$ moles $CO_2$ and stayed steady with some fluctuation possibly caused by the $CO_2$ moving in and out of solution. Due to the small reaction rate in water, only the 400 mg tablet was used.

The results of Example 3 showed the ability to create different pressure versus time profiles when the dissolution kinetics are modified.

EXAMPLE 4

The test rig was used to test silicone oil and a 27 gauge thin-wall needle. The stoichiometric reaction and results are shown in Table 4 below.

TABLE 4

| Reagents in Reaction Syringe (mg) | | Injection Syringe (mL) | Time to Deliver 1 mL silicone oil |
|---|---|---|---|
| Citric Acid | NaCl | Saturated $KHCO_3$ | (sec) |
| 140 | 200 | 0.5 | 8 |

EXAMPLE 5

The prototype test device illustrated in FIG. 19 was tested using silicone oil. A pre-filled syringe acted as the fluid chamber from which fluid was ejected. Next, a connector was used to join the pre-filled syringe with the reaction chamber. The reaction chamber included a mixing. A piece of filter paper was placed inside the reaction chamber to cover the orifice to the arm. A spring was then placed inside the mixing chamber. Next, a plunger was used to separate the dry reagent in the reaction chamber from the wet liquid. The next piece was the push button, which included an interior volume for the liquid reagent. The push button included a hole (not visible) that was used to fill the volume with liquid reagent. A screw was used to fill the hole in the push button. A cap was fitted over the push button to provide structural support, and also surrounds a portion of the reaction chamber. Finally, a thumb press was placed on top of the cap for ease of pressing. Both the reagent chamber and the reaction chamber were completely filled with liquid solution and dry powder, respectively.

The syringe was tested in both the vertical position (reagent chamber above reaction chamber) and the horizontal position (the two chambers side-by-side). The reagents and results are shown in Table 5 below.

TABLE 5

| | Reagents in Reaction Chamber (mg) | | Reagent Chamber (mL) | Time to Deliver 1 mL silicone oil |
|---|---|---|---|---|
| Orientation | Citric Acid | NaCl | Saturated $KHCO_3$ | (sec) |
| Vertical | 250 | 200 | 0.75 | 8.5 |
| Horizontal | 250 | 200 | 0.75 | 17 |

Assuming adequate mixing, the potassium bicarbonate is the limiting reactant, with citric acid at an excess of 89 mg. This assumption was found to be incorrect because liquid was found in the top chamber and powder was found in the bottom chamber when disassembled. When the syringe was laid in a horizontal position, and the chambers were completely filled, the silicone oil was displaced in 17 seconds. This illustrates that the device can work in any orientation. This is helpful for permitting patients to inject into their abdomen, thigh, or arm, which are the most common locations for self-injection.

It was noted that the push button was more difficult to press. It is believed that the mechanical design can be improved to solve this problem.

The devices and methods of the present disclosure have been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

What is claimed is:

1. A device for delivering a fluid by chemical reaction, comprising:
   a reagent chamber containing at least one of a solvent and a reagent and having a plunger at an upper end and a one-way valve at a lower end, the one-way valve permitting exit of the at least one of the solvent and the reagent from the reagent chamber;
   a reaction chamber having the one-way valve at an upper end and a piston at a lower end; and
   a fluid chamber having the piston at an upper end, wherein the piston moves in response to pressure generated in the reaction chamber such that the volume of the reaction chamber increases and the volume of the fluid chamber decreases;
   wherein the reaction chamber contains at least one of a dry powder reagent and a release agent.

2. The device of claim 1, wherein the dry powder reagent is citrate and the release agent is sodium chloride.

3. The device of claim 1, wherein a needle is fluidly connected to an outlet of the fluid chamber; and wherein the reaction chamber is located on top of the fluid chamber.

4. The device of claim 1, wherein the reagent chamber contains a first reagent and the reaction chamber contains a second reagent, and a movement of the plunger towards the one-way valve causes a mixing of the first reagent and the second reagent to initiate a gas-generating chemical reaction in the reaction chamber.

5. A device for delivering a fluid by chemical reaction, comprising:
   an upper chamber containing at least one of a solvent and a reagent and having a stationary one-way valve at a lower end, the one-way valve permitting exit of the at least one of the solvent and the reagent from the upper chamber;
   a plunger configured to travel through only the upper chamber;
   a lower chamber having the stationary one-way valve at an upper end and a piston at a lower end, the lower chamber containing at least one reagent; and
   a fluid chamber having the piston at an upper end;
   wherein a movement of the plunger towards the one-way valve causes the at least one of the solvent and the reagent to exit the upper chamber to initiate a gas-generating chemical reaction in the lower chamber, and the piston moves in response to pressure generated in the lower chamber such that the volume of the lower chamber increases and the volume of the fluid chamber decreases.

6. The device of claim 5, wherein the fluid chamber contains a high-viscosity fluid having a viscosity of at least 40 centipoise.

7. The device of claim 5, wherein the upper chamber contains only the solvent and the lower chamber contains at least two reagents.

8. The device of claim 5, wherein the plunger includes a thumbrest and a pressure lock that cooperates with the upper chamber to lock the plunger in place after being depressed.

9. The device of claim 8, wherein the pressure lock is proximate the thumbrest and cooperates with an upper surface of the upper chamber.

10. The device of claim 5, wherein the lower chamber is defined by the one-way valve, a continuous sidewall, and the piston, the one-way valve and the sidewall being fixed relative to each other such that the volume of the lower chamber changes only through movement of the piston.

11. The device of claim 5, wherein the upper chamber, the lower chamber, and the fluid chamber are cylindrical and are coaxial.

12. The device of claim 5, wherein the upper chamber, the lower chamber, and the fluid chamber are separate pieces that are joined together to make the device.

13. The device of claim 5, wherein the upper chamber contains a first reagent and the lower chamber contains a second reagent, and a movement of the plunger towards the one-way valve causes a mixing of the first reagent and the second reagent to initiate a gas-generating chemical reaction in the lower chamber.

* * * * *